US012643924B2

(12) United States Patent
Zahid

(10) Patent No.: US 12,643,924 B2
(45) Date of Patent: Jun. 2, 2026

(54) CARDIAC-SPECIFIC TARGETING-PEPTIDE (CTP), COMPOSITIONS, AND USES THEREOF

(71) Applicant: University of Pittsburgh—Of the Commonwealth System of Higher Education, Pittsburgh, PA (US)

(72) Inventor: Maliha Zahid, Gibsonia, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 178 days.

(21) Appl. No.: 18/303,093

(22) Filed: Apr. 19, 2023

(65) Prior Publication Data

US 2023/0406882 A1     Dec. 21, 2023

Related U.S. Application Data

(63) Continuation of application No. 17/056,193, filed as application No. PCT/US2019/033551 on May 22, 2019, now abandoned.

(60) Provisional application No. 62/811,077, filed on Feb. 27, 2019, provisional application No. 62/778,033, filed on Dec. 11, 2018, provisional application No. 62/675,307, filed on May 23, 2018.

(51) Int. Cl.
*C07K 7/08*     (2006.01)
*A61K 38/00*     (2006.01)

(52) U.S. Cl.
CPC ............... *C07K 7/08* (2013.01); *A61K 38/00* (2013.01); *C07K 2319/10* (2013.01); *C07K 2319/60* (2013.01); *C12Y 114/99003* (2013.01)

(58) Field of Classification Search
CPC .. C07K 7/08; C07K 2319/10; C07K 2319/60; C07K 2319/00; C07K 7/06; A61K 38/00; A61K 9/0019; C12Y 114/99003; G01N 33/582; A61P 9/06; A61P 39/06
See application file for complete search history.

(56) References Cited

U.S. PATENT DOCUMENTS

| | | | |
|---|---|---|---|
| 5,911,983 A | 6/1999 | Barranger et al. | |
| 6,063,576 A * | 5/2000 | Keating ............. | C07K 14/4716 435/7.1 |
| 8,618,061 B2 | 12/2013 | Szeto | |
| 9,249,184 B2 * | 2/2016 | Robbins ................... | C07K 7/06 |
| 9,550,981 B2 * | 1/2017 | Chin ................... | C07K 14/005 |
| 2002/0061299 A1 | 5/2002 | French | |
| 2003/0219497 A1 | 11/2003 | Otterbein et al. | |
| 2005/0112128 A1 | 5/2005 | McKinsey et al. | |
| 2006/0084606 A1 | 4/2006 | Szeto | |
| 2010/0221235 A1 | 9/2010 | Arranz | |
| 2010/0310495 A1 | 12/2010 | Schneider et al. | |

| | | | |
|---|---|---|---|
| 2012/0009193 A1 * | 1/2012 | Brown ................... | A61P 29/00 424/139.1 |
| 2012/0244136 A1 | 9/2012 | Robbins et al. | |
| 2012/0277158 A1 | 11/2012 | Castaigne et al. | |
| 2015/0297742 A1 | 10/2015 | Strieker et al. | |
| 2015/0307582 A1 | 10/2015 | Xu et al. | |
| 2015/0328315 A1 * | 11/2015 | Kalifa ................... | A61K 38/20 424/9.1 |
| 2016/0106800 A1 | 4/2016 | Szeto et al. | |

FOREIGN PATENT DOCUMENTS

| | | | | |
|---|---|---|---|---|
| CN | 102766258 A | 11/2012 | | |
| WO | WO-2003/079972 A2 | 10/2003 | | |
| WO | WO-2008/045976 A2 | 4/2008 | | |
| WO | WO-2010033868 A2 * | 3/2010 | .......... | C07K 14/005 |
| WO | WO-2018/090042 A1 | 5/2018 | | |

OTHER PUBLICATIONS

Zimetbaum, Amiodarone for Atrial Fibrillation, n engl j med 356;9:935-941. (Year: 2007).*
Claro, JC, Candia, R, Rada, G, Baraona, F, Larrondo, F, Letelier, LM., Amiodarone versus other pharmacological interventions for prevention of sudden cardiac death. Cochrane Database of Systematic Reviews 2015, Issue 12. Art. No. CD008093. DOI: 10.1002/14651858.CD008093.pub2. (Year: 2015).*
Bhat et al., Lead discovery and optimization strategies for peptide macrocycles, European Journal of Medicinal Chemistry 94 (2015) 471e479. http://dx.doi.org/10.1016/j.ejmech.2014.07.083 (Year: 2015).*
NlpCP60 family protein [*Lactobacillus* sp HT06-2]—Protein—NCBI, PDF generated using Adobe plugin in google chrome from the following website: https://www.ncbi.nlm.nih.gov/protein/WP_103661436.1?report=genbank&log$=protalign&blast_rank=3&RID=FP2SCZJW013 (Year: 2024).*
Montigiani et al., J. Mol. Biol. (1996) 258, 6-13 (Year: 1996).*
Morrison and Weiss, Current Opinion in Chemical Biology 2001, 5:302-307 (Year: 2001).*
Ngambenjawong et al., Bioconjugate Chem. 2016, 27, 2854-2862 (Year: 2016).*
Gunasekera et al., ChemBioChem 2018, 19, 931-939 (Year: 2018).*
Alanine Scan—Mimotopes—archive image, Published 2012, Examiner generated PDF; https://web.archive.org/web/ 20161106145413/http://www. mimotopes .com/peptideLibraryScreening .asp?id =94 (Year: 2012).

(Continued)

*Primary Examiner* — Joseph Fischer
(74) *Attorney, Agent, or Firm* — Goodwin Procter LLP

(57) ABSTRACT

Disclosed is a synthetic, non-naturally occurring 12-amino acid peptide, Cardiac Targeting Peptide, belonging to the larger class of cell penetrating peptides, for delivery of both diagnostic and potentially therapeutic agents to the heart. Also disclosed are subsequent generations of this Cardiac Targeting Peptide with improved, higher efficiency of cardiac uptake for CTP-mediated delivery of antiarrhythmics subjects for treating Atrial fibrillation or Ventricular fibrillation, CTP-mediated delivery of neuregulin-1β for treating systolic heart failure (SHF), and Szeto-Schiller peptides for treatment of diastolic congestive heart failure, among other applications.

8 Claims, 14 Drawing Sheets

Specification includes a Sequence Listing.

(56)         References Cited

OTHER PUBLICATIONS

Arap et al., "Cancer Treatment by Targeted Drug Delivery to Tumor Vasculature in a Mouse Model", Science, 279(5349):377-380, Jan. 1998.

Castel et al. (2011) "Phage Display of Combinatorial Peptide Libraries: Application to Antiviral Research," Molecules 16:3499-3518.

Frantz et al., "Absence of NF-κb Subunit p50 Improves Heart Failure after Myocardial Infarction", The FASEB Journal, 20(11):1918-1920, Sep. 2006.

Jiang et al., "Acute Protection of Ischemic Heart by FGF-2: Involvement of FGF-2 Receptors and Protein Kinase C", Am J Physiol Heart Circ Physiol, 282(3):H1071-H1080, Mar. 2002.

Kamide et al. (2010) "Isolation of novel cell-penetrating peptides from a random peptide library using in vitro virus and their modifications," International Journal of Molecular Medicine 25:41-51.

Kawano et al., "Blockade of NF-κb Improves Cardiac Function and Survival after Myocardial Infarction", Am. J Physiol Heart Circ Physiol, 291:H1337-H1344, 2006.

Kelly et al., "In Vivo Phage Display Selection Yields Atherosclerotic Plaque Targeted Peptides for Imaging", Molecular Imaging and Biology, 8(4):201-207, 2006.

Li et al., "Gene Therapy with Extracellular Superoxide Dismutase Protects Conscious Rabbits Against Myocardial Infarction", Circulation, 103(14):1893-1898, Apr. 2001.

Li et al., "Gene Therapy with iNOS Provides Long-Term Protection Against Myocardial Infarction Without Adverse Functional Consequences", Am J Physiol Heart Circ Physiol, 290(2):H584-H589, Feb. 2006.

Lu et al., "Targeting of Embryonic Stem Cells by Peptide-Conjugated Quantum Dots", PloS One, 5(8):e12075, Aug. 2010.

McGuire et al., "In vitro Selection of a Peptide with High Selectivity for Cardiomyocytes In vivo", Journal of Molecular Biology, 342(1):171-182, Sep. 2004.

Melo et al., "Gene Therapy Strategy for Long-Term Myocardial Protection Using Adena-Associated Virus-Mediated Delivery of Heme Oxygenase Gene", Circulation, 105(5):602-607, Feb. 2002.

Mi et al., "Identification of a Synovial Fibroblast-Specific Protein Transduction Domain for Delivery of Apoptotic Agents to Hyperplastic Synovium", Molecular Therapy, 8(2):295-305, Aug. 2003.

Molenaar et al., "Uptake and Processing of Modified Bacteriophage M13 in Mice: Implications for Phage Display", Virology, 293(1):182-191, Feb. 2002.

Okada et al., "Postinfarction Gene Therapy Against Transforming Growth Factor-β signal Modulates Infarct Tissue Dynamics and Attenuates Left Ventricular Remodeling and Heart Failure", Circulation, 111(19):2430-2437, May 2005.

Pachori et al. (2004) "Hypoxia-regulated Therapeutic Gene as a Preemptive Treatment Strategy Against Ischemia/Reperfustion Injury," PNAS 101(33):12282-12287.

Pasqualini et al., "Organ Targeting In Vivo Using Phage Display Peptide Libraries", Nature, 380(6572):364-366, Mar. 1996.

Pleger et al., "S100Al Gene Therapy Preserves in Vivo Cardiac Function after Myocardial Infarction", Molecular Therapy, 12(6):1120-1129, Dec. 2005.

Positional Scan—Mimotopes—Archive image, Published 2016, Examiner generated PDF; https://web.archive.org/web/20160412054617/http://www.mimotopes.com/peptideLibraryScreening.asp?id =92 (Year: 2016).

Rogers et al., "Temporal Trends in the Treatment of Over 1.5 Million Patients With Myocardial Infarction in the U.S. from 19990 Through 1999: The National Registry of Myocardial Infarction 1, 2 and 3", Journal of the American College of Cardiology, 36(7):2056-2063, Dec. 2000.

Roncalli et al., "Sonic Hedgehog-Induced Functional Recovery After Myocardial Infarction Is Enhanced by AMD3100-Mediated Progenitor-Cell Mobilization", Journal of the American College of Cardiology, 57(24):2444-2452, Jun. 2011.

Rákos et al., "Evans Blue Fluorescence Permits the Rapid Visualization of Non-Intact Cells in the Perilesional Rim of Cold-Injured Rat Brain", Acta Neurobiologiae Experimentals (Wars.), 67(2):149-154, 2007.

Segvich et al., "Identification of Peptides with Targeted Adhesion to Bone-Like Mineral via Phage Display and Computational Modeling", Cells Tissue Organs, 189(1-4):245-251, 2009.

Segvich et al., "The Absorption of Preferential Binding Peptides to Apatite-Based Materials", Biomaterials, 30(7):1287-1298, Mar. 2009.

Szeto HH, (2006) "Cell-permeable, Mitochondrial-targeted, Peptide Antioxidants," The AAPS Journal 8(2):E277-E283.

Traboulsi et al. (2015) "Macrocyclic Cell Penetrating Peptides: A Study of Structure-Penetration Properties," Bioconjugate Chemistry 26(3):405-411.

Truncation—Mimotopes—archive image, Published 2012, Examiner generated PDF; https://web.archive.org/web/20161106145333/http://www.mimotopes.com/peptideLibraryScreening.asp?id =91 (Year: 2012).

Wiviott et al., "Performance of the Thrombolysis In Myocardial Infarction Risk Index in the National Registry of Myocardial Infarction-3 and -4: A Simple Index That Predicts Mortality in ST-Segment Elevation Myocardial Infarction", Journal of the American College of Cardiology, 44(4):783-789, Aug. 2004.

Written Opinion for International Application No. PCT/US2019/033551 dated Oct. 24, 2019.

Yao et al., "Targeting Pancreatic Islets with Phage Display Assisted by Laser Pressure Catapult Microdissection", American Journal of Pathology, 166(2):625-636, Feb. 2005.

Zahid et al., Aug. 17, 2010, Identification of a Cardiac Specific Protein Transduction Domain by In Vivo Biopanning using a M 13 Phage peptide Display Library in Mice, PLoS One, 5(8): 11 pages.

Zahid, 2009, Targeting the Heart Using In Vivo Phage Display, University of Pittsburgh, Doctoral thesis, 132 pages.

Zahid, et al. (2016) "Targeting the Heart Utilizing a Novel Cell Penetrating Peptide," International Academy of Cardiology, Annual Scientific Sessions 2016 21st World Congress on Heart Disease. Conference Abstract (Online) p. 42.

Zahid, et al. (2017) "A Novel Cell Penetrating Peptide, Cardiac Targeting Peptide Appears to Utilize Cardiac Channels for Transduction." International Academy of Cardiology, Annual Scientific Sessions 2017 22nd World Congress on Heart Disease. Conference abstract (online) p. 40.

Zhang et al., "Molecular Profiling of Heart Endothelial Cells", Circulation, 112(11):601-611, Sep. 2005.

Lu, M. et al. "Reversing cardiac hypertrophy and heart failure using a cardiac targeting peptide linked to miRNA106a," Clin. Transl. Med., 15:e70432, 22 pages (2025).

* cited by examiner

CARDIAC-SPECIFIC TARGETING-PEPTIDE (CTP), COMPOSITIONS, AND USES THEREOF

CROSS-REFERENCE TO RELATED APPLICATIONS

This application is a continuation patent application of U.S. patent application Ser. No. 17/056,193, filed Nov. 17, 2020, which is a U.S. national stage application, filed under 35 U.S.C. § 371, of International Application No. PCT/US2019/033551, filed on May 22, 2019, which claims the benefit of and priority to U.S. Provisional Patent Application No. 62/675,307, filed May 23, 2018; U.S. Provisional Patent Application No. 62/778,033, filed Dec. 11, 2018; and U.S. Provisional Patent Application No. 62/811,077, filed Feb. 27, 2019; the disclosures of each of which is hereby incorporated by reference in their entirety for all purposes.

SEQUENCE LISTING

The present specification makes reference to a Sequence Listing which has been submitted electronically in XML format and is hereby incorporated by reference in its entirety. Said XML file, created on Apr. 19, 2023, is named UPB-013USC1_ST26.xml and is 46 kilobytes in size.

FIELD OF THE INVENTION

The invention relates generally to cardiac-specific targeting peptides (CTP)-mediated delivery of moieties having antiarrhythmic properties for treating Atrial fibrillation or Ventricular fibrillation, and CTP-mediated delivery of neuregulin-1β for treating systolic heart failure (SHF). The invention also relates generally to cardiac-specific targeting peptide (CTP$_{6aa}$), compositions of CTP$_{6aa}$, use of the CTP$_{6aa}$ or a composition thereof in methods of treating cardiac conditions, and use of CTP$_{6aa}$ in delivering molecular cargoes specifically to cells of the heart.

BACKGROUND

Atrial fibrillation (also called AFib or AF) is a quivering or irregular heartbeat (arrhythmia) that can lead to blood clots, stroke, heart failure and other heart-related complications. At least 2.7 million Americans are living with AFib. Ventricular fibrillation (VFib) is a serious cardiac disturbance that is a life-threatening rhythm and a common cause of sudden cardiac death. It can be fatal. For many people with this condition, irregular heart rhythms are the first and only sign of coronary artery disease. VFib and AFib involve irregular heart rhythms, but they affect different parts of the heart. AFib can also signal a serious heart condition, but it is typically a symptom of a chronic problem, not a life-threatening feature in itself (source: American Heart Association).

One of the most effective pharmaceutical therapies for AFib and VFib, amiodarone, has significant systemic toxicities leading to reduced long-term utilization of the drug. The present disclosure addresses an unmet medical need for targeted delivery of cardiac therapeutics for treating AFib and/or VFib by delivering therapeutic agents directly to cardiomyocytes, thereby reducing off-target effects and increasing the use of existing, effective therapies.

A protein transduction peptide specific for the heart would be able to deliver biologic agents in a timely fashion to the heart when given at the time of reperfusion for an infarction:

Protein transduction domains (PTD) are small cationic peptides that can cross cellular membranes, and are able to transport large, biologically active molecules into mammalian cells in culture as well as in vivo. The limitation of PTDs is the non-specific transduction of all tissue types with some tissues, such as liver and kidney, taking up the PTD much more avidly than heart tissue. Thus there is a need to identify peptides able to target cardiac tissue specifically for delivery of biologics of therapeutic potential.

Although developments have been made to date, there is still an ongoing need for new and effective peptides able to target cardiac tissue specifically for delivery of biologics and/or cargo of therapeutic potential.

SUMMARY OF THE INVENTION

In one aspect, the present disclosure provides a peptide comprising a twelve amino acid Cardiac-specific Targeting-Peptide (CTP$_{12aa}$) having a sequence of Ala-Pro-Trp-His-Leu-Ser-Ser-Gln-Tyr-Ser-Arg-Thr (SEQ ID NO: 1), a six amino acid CTP (CTP$_{6aa}$) having a sequence of SQYSRT (SEQ ID NO: 5), or a twelve amino acid CTP having a sequence of AAWHLSSQYSRT (SEQ ID NO: 2 (CTP-P2A)) linked to a moiety having antiarrhythmic properties (for example, amiodarone (IUPAC name: (2-butyl-1-benzofuran-3-yl)-[4-[2-(diethylamino)ethoxy]-3,5-diiodophenyl] methanone; molecular formula: $C_{25}H_{29}I_2NO_3$)). In some embodiments, the moiety having antiarrhythmic properties (for example, amiodarone) is linked upstream of the N-terminus of the CTP (CTP$_{12aa}$, CTP$_{6aa}$, or CTP-P2A).

In one aspect, a peptide comprising a CTP of SEQ ID NO: 1, 2, 4, 5, 6, 7, 8, 9, 10, 11, 28, 29, or 34 is linked to a moiety having antiarrhythmic properties. Moieties with antiarrhythmic properties include compounds that can be grouped into 4 main classes of antiarrhythmics (classes I, II, III, and IV) under the Vaughan Williams classification scheme. The Vaughan Williams classification scheme categorizes antiarrhythmics according to their dominant cellular electrophysiologic effect and mechanism of action.

Class I compounds include sodium channel blockers (membrane-stabilizing drugs) that can block fast sodium channels, slowing conduction in fast-channel tissues (for example, in working atrial and ventricular myocytes, and in the His-Purkinje system). Class I compounds can be subdivided into subclasses a, b, and c, with subclass a compounds (for example, anticholinergics such as quinidine, procainamide, and disopyramide) having moderate effects, subclass b compounds (for example, lidocaine and lidocaine analogs, including tocainide and mexiletine) having weak effects, and subclass c compounds (for example, flecainide, propafenone, and moricizine) having strong effects.

Class II compounds include beta-blockers, which can affect predominantly slow-channel tissues (for example, sinoatrial (SA) and atrioventricular (AV) node tissues), by decreasing rate of automaticity, slowing conduction velocity, and prolonging refractoriness. Examples of class II compounds include: carteolol, carvedilol, labetalol, nadolol, penbutolol, pindolol, propranolol, sotalol, timolol, acebutolol, atenolol, betaxolol, bisoprolol, esmolol, metoprolol, and nebivolol.

Class III compounds include potassium channel blockers, which can prolong action potential duration and refractoriness in slow-channel and fast-channel tissues. Examples of class III compounds include: amiodarone, dronedarone, bretylium, sotalol, ibutilide, and dofetilide.

Class IV compounds include calcium channel blockers, for example, the dihydropyridine and non-dihydropyridine calcium channel blockers, that can depress calcium-dependent action potentials in slow-channel tissues, decreasing the rate of automaticity, slowing conduction velocity, and prolonging refractoriness.

Class IV dihydropyridine compounds include: amlodipine, felodipine, isradipine, nicardipine, nifedipine, nimodipine, and nitrendipine. Class IV non-dihydropyridine compounds include: verapamil and diltiazem.

Moieties described herein having antiarrhythmic properties include active pharmaceutical compounds classified as class I antiarrhythmics, class II antiarrhythmics, class III antiarrhythmics, and class IV antiarrhythmics. Exemplary antiarrhythmics conjugated to a CTP of the present disclosure include: amiodarone (synonyms: Amiodarona, Amiodaronum, Cordarone, Pacerone), flecainide (Tambocor), ibutilide (Corvert), lidocaine (Xylocaine), procainamide (Procan, Procanbid), propafenone (Rythmol), quinidine, and tocainide (Tonocarid). For example, in some embodiments the disclosure provides a method of treating an atrial arrhythmia and/or a ventricular arrhythmia (for example, premature ventricular contractions, ventricular tachycardia, atrial fibrillation, or ventricular fibrillation), where the method includes administering a peptide comprising a CTP (for example, a CTP of SEQ ID NO: 1, 2, 4, 5, 6, 7, 8, 9, 10, 11, 28, 29, or 34) linked to amiodarone to a patient, for example, a patient in need of treatment.

In certain embodiments a peptide comprising a CTP of SEQ ID NO: 1 is linked to a moiety having antiarrhythmic properties, for example amiodarone, and used in a method of treating cardiac tissue or a cardiac condition in a subject in need thereof. In certain embodiments a peptide comprising a CTP of SEQ ID NO: 2 is linked to a moiety having antiarrhythmic properties, for example amiodarone, and used in a method of treating cardiac tissue or a cardiac condition in a subject in need thereof. In certain embodiments a peptide comprising a CTP of SEQ ID NO: 5 is linked to a moiety having antiarrhythmic properties, for example amiodarone, and used in a method of treating cardiac tissue or a cardiac condition in a subject in need thereof. In certain embodiments, the cardiac condition is an atrial arrhythmia, for example, atrial fibrillation. In certain embodiments, the cardiac condition is a ventricular arrhythmia, for example, ventricular tachycardia.

In one aspect, a peptide comprising a CTP of SEQ ID NO: 1, 2, 4, 5, 6, 7, 8, 9, 10, 11, 28, 29, or 34 is linked to Neuregulin-1β, and used in a method of treating cardiac tissue or a cardiac condition in a subject in need thereof. In certain embodiments, the cardiac condition is systolic heart failure (SHF). Thus, in some embodiments the disclosure provides a method of treating heart failure, for example, SHF, where the method includes administering a peptide comprising a CTP (for example, a CTP of SEQ ID NO: 1, 2, 4, 5, 6, 7, 8, 9, 10, 11, 28, 29, or 34) linked to Neuregulin-1β to a patient, for example, a patient in need of treatment.

In one aspect the invention provides a peptide comprising a $CTP_{6aa}$ comprising the sequence of $Xaa_1$ $Xaa_2$ Y $Xaa_3$ $Xaa_4$ T (SEQ ID NO: 4), in which $Xaa_1$, $Xaa_2$, $Xaa_3$, and $Xaa_4$ is any naturally occurring amino acid, linked to a moiety having antiarrhythmic properties, for example amiodarone, or to Neuregulin-1β. In some embodiments, a moiety having antiarrhythmic properties or Neuregulin-1β is linked upstream of the N-terminus of the $CTP_{6aa}$. In certain embodiments, $Xaa_1$ in the $CTP_{6aa}$ of SEQ ID NO: 4 is serine (S). In certain embodiments, $Xaa_2$ in the $CTP_{6aa}$ of SEQ ID NO: 4 is glutamine (Q). In certain embodiments, $Xaa_3$ in the $CTP_{6aa}$ of SEQ ID NO: 4 is serine (S). In certain embodiments, $Xaa_4$ in the $CTP_{6aa}$ of SEQ ID NO: 4 is arginine (R). In certain embodiments, $Xaa_1$ and $Xaa_2$ in the $CTP_{6aa}$ of SEQ ID NO: 4 are serine (S) and glutamine (Q), respectively. In certain embodiments, $Xaa_1$ and $Xaa_3$ in the $CTP_{6aa}$ of SEQ ID NO: 4 are both serine (S). In certain embodiments, $Xaa_1$ and $Xaa_4$ in the $CTP_{6aa}$ of SEQ ID NO: 4 are serine (S) and arginine (R), respectively. In certain embodiments, $Xaa_2$ and $Xaa_3$ in the $CTP_{6aa}$ of SEQ ID NO:4 are glutamine (Q) and serine (S), respectively. In certain embodiments, the $CTP_{6aa}$ comprises the sequence SQYSRT (SEQ ID NO: 5). In certain embodiments, a peptide comprising a $CTP_{6aa}$ comprising the sequence of $Xaa_1$ $Xaa_2$ W $Xaa_3$ $Xaa_4$ T (SEQ ID NO: 23), in which $Xaa_1$, $Xaa_2$, $Xaa_3$, and $Xaa_4$ is any naturally occurring amino acid, is linked to a moiety having antiarrhythmic properties, for example amiodarone, or to Neuregulin-1β.

In one aspect the invention provides a peptide comprising a $CTP_{6aa}$ a comprising the sequence of S Q $Xaa_1$ S R $Xaa_2$ (SEQ ID NO: 6) linked to a moiety having antiarrhythmic properties, for example, amiodarone. In some embodiments, a moiety having antiarrhythmic properties, for example amiodarone, is linked upstream of the N-terminus of the $CTP_{6aa}$ a.

In one aspect the invention provides a peptide comprising a $CTP_{6aa}$ a comprising the sequence of S Q $Xaa_1$ S R $Xaa_2$ (SEQ ID NO: 6) linked to Neuregulin-1β. In some embodiments, Neuregulin-1β is linked upstream of the N-terminus of the $CTP_{6aa}$.

In certain embodiments, $Xaa_1$ in the $CTP_{6aa}$ of SEQ ID NO: 6 is alanine (A) and the $CTP_{6aa}$ comprises the sequence of $SQASRXaa_2$ (SEQ ID NO: 7), or optionally, $Xaa_1$ in the $CTP_{6aa}$ of SEQ ID NO: 6 is tryptophan (W) and the $CTP_{6aa}$ comprises the sequence of $SQWSRXaa_2$ (SEQ ID NO: 8), or $Xaa_1$ in the $CTP_{6aa}$ of SEQ ID NO: 6 is tyrosine (Y) and the $CTP_{6aa}$ comprises the sequence of $SQYSRXaa_2$ (SEQ ID NO: 9). In certain embodiments, $Xaa_2$ in the $CTP_{6aa}$ of SEQ ID NO: 6 is threonine (T), and $Xaa_1$ in the $CTP_{6aa}$ of SEQ ID NO: 6 is alanine (A), tryptophan (W), or tyrosine (Y) comprising the sequence of SQASRT (SEQ ID NO: 10), SQWSRT (SEQ ID NO: 11), or SQYSRT (SEQ ID NO: 5), respectively. In certain embodiments, $Xaa_2$ in the $CTP_{6aa}$ of SEQ ID NO: 6 is alanine (A). In certain embodiments, $Xaa_1$ in the $CTP_{6aa}$ of SEQ ID NO: 6 is tyrosine (Y) and $Xaa_2$ is alanine (A). In certain embodiments, the $CTP_{6aa}$ comprises the sequence SQYSRT (SEQ ID NO: 5).

In certain embodiments, a peptide comprising a $CTP_{6aa}$ of SEQ ID NO: 4 and SEQ ID NO: 6, for example SEQ ID NO: 5, is a recombinant or synthetically prepared peptide.

In some embodiments, a second peptide sequence, protein, or small molecule is linked upstream of the N-terminus of the CTP ($CTP_{12aa}$, $CTP_{6aa}$, or CTP-P2A). In some embodiments the linked peptide can include an ester linkage between the CTP and the second peptide sequence, protein, or small molecule, and the ester linkage can only be cleaved by an intracellular esterase.

In some embodiments, a peptide comprising a CTP ($CTP_{12aa}$, $CTP_{6aa}$, or CTP-P2A) linked to a moiety having antiarrhythmic properties, for example amiodarone, is optionally further labelled at both the C- and N-termini. For example, in some embodiments, the peptide is labelled with a green fluorescent moiety, for example, 6-carboxyfluorosceine, and a red fluorescent moiety, for example, Cy5.5. For example, in some embodiments, the peptide is labelled with a green fluorescent moiety at its N-terminus and a red fluorescent moiety at its C-terminus. In some embodiments, the peptide is labelled with a red fluorescent moiety at its N-terminus and a green fluorescent moiety at its C-terminus.

It is contemplated that any of the foregoing CTP peptides of SEQ ID NOs: 1-35 may, for example, be conjugated to a water-soluble polymer, e.g., polyethylene glycol (PEG). In certain embodiments, the $CTP_{6aa}$ of SEQ ID NO: 5 is conjugated to a water-soluble polymer, e.g., polyethylene glycol (PEG).

In another aspect, the invention provides an isolated nucleic acid comprising a nucleotide sequence encoding any one of the foregoing CTP peptides of SEQ ID NOs: 1-35. In certain embodiments, the nucleotide sequence is codon optimized for expression in a host cell, e.g., an *Escherichia coli* cell. The invention also provides an expression vector that comprises any one of the foregoing nucleotide sequences. Similarly, the invention provides host cells, e.g., *Escherichia coli* cells, comprising one or more of the foregoing expression vectors. The peptide can be produced in isolation in expression vectors or as a fusion peptide/protein at the C-terminus of the peptide/protein to be delivered, either with an intervening ester linkage or in continuity.

In another aspect, the invention provides a pharmaceutical composition comprising a peptide and any variants of any one of SEQ ID NOs: 1-35, and at least one pharmaceutically acceptable carrier and/or an excipient. The peptide may be in a soluble form or in a crystal form. Furthermore, the composition may comprise a pH increasing agent. It is contemplated that the pharmaceutical composition may, for example, be formulated as an oral dosage form or a parenteral dosage form. In certain embodiments, the composition is formulated as a powder, granulate, pellet, micropellet, or a minitablet that can be orally administered, or as a lyophilized powder that can be reconstituted in normal saline or deiodized water for intravenous injection.

These and other aspects and features of the invention are described in the following detailed description and claims.

BRIEF DESCRIPTION OF THE DRAWINGS

The invention can be more completely understood with reference to the following drawings.

FIG. 2A shows the transduction of H9C2 cells in a first experiment. FIG. 2B shows the transduction of H9C2 cells in a second experiment. FIG. 2C shows the transduction of H9C2 cells and MEF cells. FIG. 2D shows the transduction of H9C2 and 3T3 cells. FIG. 2E shows the viability of H9C2 cells and MEF cells transduced with the Cy5.5 labeled cardiac-specific targeting peptide variants. CTP (Full Length): $NH_2$-APWHLSSQYSRT-COOH (SEQ ID NO: 1); CTP-A: $NH_2$-APWHLS-COOH (SEQ ID NO: 24); CTP-B: $NH_2$-SQYSRT-COOH ($CTP_{6aa}$; SEQ ID NO: 5); cyclic: cyclized version of the indicated peptide; CTP-Random: random, linear, 12-amino acid peptide (RAN: $NH_2$-STLMKFCYVEQN-COOH ((SEQ ID NO: 26)); DMSO: Dimethyl sulfoxide.

and rhodamine (red) cardiac-specific targeting peptide was performed. iPSC derived cardiomyocytes showed staining for troponin (FIG. 3A), calcium transients (FIG. 3B), and robust delivery of the rhodamine cargo, while the carboxyfluorescein conjugated to the N-terminus of CTP appears to be released/secreted from the cells (FIG. 3C). FIG. 3D is a dark-field image of the cell architecture. Scale bars represent 30 μm.

DETAILED DESCRIPTION

Figure 1A:
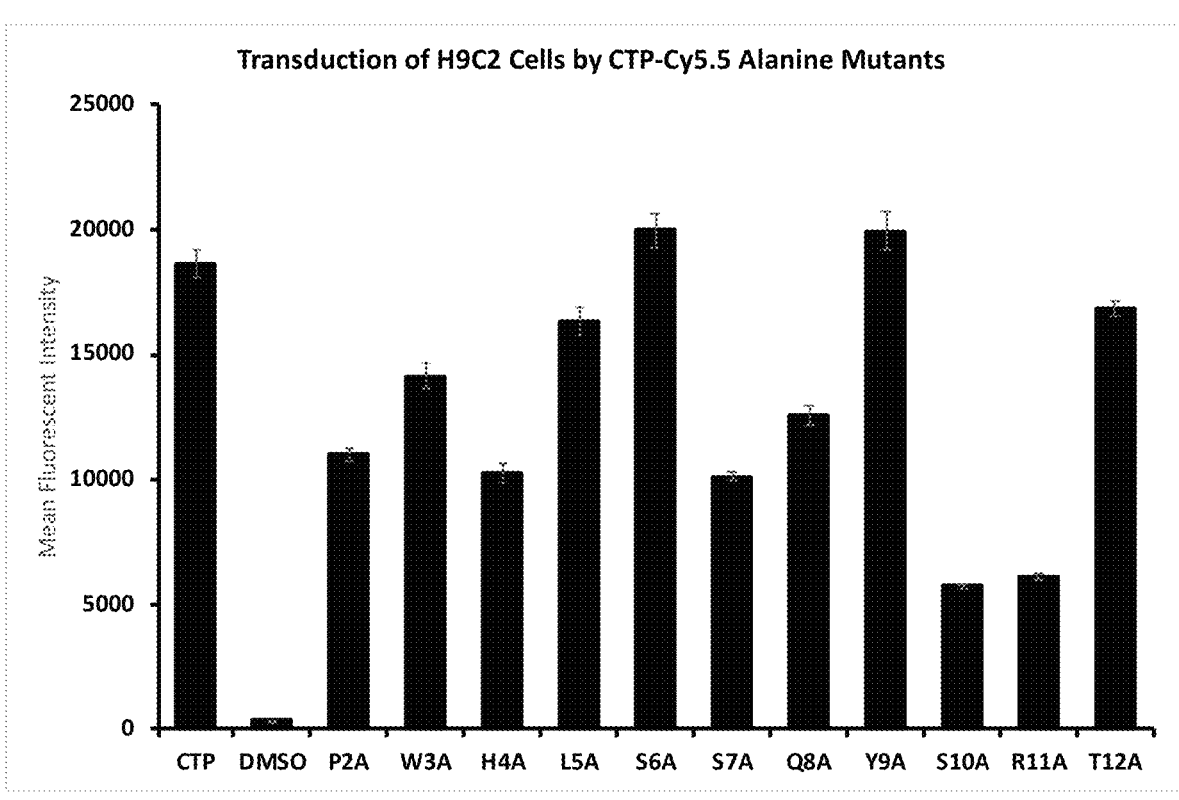
FIG. 1A, FIG. 1B, FIG. 1C, and FIG. 1D are bar graphs that quantify the fluorescence intensity of H9C2 cells transduced with cardiac-specific targeting peptide alanine mutants labeled with Cy5.5. The sequence for each indicated alanine mutant is provided in Table 2.

The invention is based, in part, upon the unexpected discovery of a six amino acid cardiac-specific targeting-peptide ($CTP_{6aa}$) with efficient cardiac-tissue specific transduction/cell penetration property, and, in effect, efficient cardiac-tissue specific cargo-delivery and therapeutic properties. The $CTP_{6aa}$ of the present disclosure has fewer amino acids than the full-length CTP described in U.S. Pat. No. 9,249,184, and, therefore, would be less immunogenic than the full-length CTP. The present disclosure provides that the $CTP_{6aa}$ of the present disclosure would be advantageous, compared to the full-length CTP or an N-terminus fragment of the CTP, in delivering a cargo and/or a therapeutic agent to the cardiac tissue of a mammalian subject (e.g., human).

Various features and aspects of the invention are discussed in more detail below.

In certain embodiments, the present disclosure provides a CTP peptide of Table 1 herein below, linked to a therapeutic moiety for treating a cardiac disease and/or condition.

TABLE 1

| SEQ ID NO: | Sequence of CTP6aa of the present disclosure |
|---|---|
| 1 | APWHLSSQYSRT |
| 2 | AAWHLSSQYSRT (CTP-P2A) |
| 3 | Amiodarone-SQYSRT (CTP-B) |
| 4 | $Xaa_1$ $Xaa_2$ Y $Xaa_3$ $Xaa_4$ T |
| 5 | SQYSRT (CTP-B) |
| 6 | S Q $Xaa_1$ S R $Xaa_2$ |
| 7 | SQASR$Xaa_2$ |
| 8 | SQWSR$Xaa_2$ |
| 9 | SQYSR$Xaa_2$ |

7

TABLE 1-continued

| SEQ ID NO: | Sequence of CTP6aa of the present disclosure |
|---|---|
| 10 | SQASRT |
| 11 | SQWSRT |
| 12 | S Xaa$_2$ Y Xaa$_3$ Xaa$_4$ T |
| 13 | Xaa$_1$ Q Y Xaa$_3$ Xaa$_4$ T |
| 14 | Xaa$_1$ Xaa$_2$ Y S Xaa$_4$ T |
| 15 | Xaa$_1$ Xaa$_2$ Y Xaa$_3$ R T |
| 16 | S Q Y Xaa$_3$ Xaa$_4$ T |
| 17 | S Xaa$_2$ Y S Xaa$_4$ T |
| 18 | S Xaa$_2$ Y Xaa$_3$ R T |
| 19 | Xaa$_1$ Q Y S Xaa$_4$ T |
| 20 | S Xaa$_2$ Y S R T |
| 21 | Xaa$_1$ Q Y S R T |
| 22 | S Q Y Xaa$_3$ R T |
| 23 | Xaa$_1$ Xaa$_2$ W Xaa$_3$ Xaa$_4$ T |
| 24 | APWHLS (CTP-A) |
| 25 | Amiodarone-AAWHLSSQYSRT (CTP-P2A) |
| 26 | H4A APWALSSQYSRT |
| 27 | L5A APWHASSQYSRT |
| 28 | S6A APWHLASQYSRT |
| 29 | S7A APWHLSAQYSRT |
| 30 | Q8A APWHLSSAYSRT |
| 31 | Y9A APWHLSSQASRT |
| 32 | S10A APWHLSSQYART |
| 33 | R11A APWHLSSQYSAT |
| 34 | T12A APWHLSSQYSRA |
| 35 | W3A APAHLSSQYSRT |

The CTP of any one of SEQ ID NOs: 1-35 is a recombinant or synthetically prepared peptide.

I. Six Amino Acid Cardiac-Specific Targeting-Peptide (CTP$_{6aa}$)

The present disclosure provides for Cardiac Targeting Peptides ("CTP"). In certain non-limiting embodiments the CTP specifically targets cardiac tissue. "Specifically targets cardiac tissue" means that when said CTP, linked to a cargo molecule to form a CTP-cargo complex, is injected into a mammal, the CTP-cargo complex is transduced into cardiac tissue at much higher levels than it is transduced into other tissues, such as, for example, liver, kidney, lung, skeletal muscle, or brain. In certain embodiments the ratio of transduction of a CTP that "specifically targets cardiac tissue" into cardiac tissue relative to liver, kidney, lung, skeletal muscle or brain is at least 2:1 or is at least 3:1.

In one aspect the invention is based, in part, upon the discovery of a six amino acid Cardiac-specific Targeting-Peptide (CTP$_{6aa}$) comprising the sequence of Xaa$_1$ Xaa$_2$Y Xaa$_3$ Xaa$_4$ T (SEQ ID NO: 4). In certain embodiments, Xaa$_1$ in the CTP$_{6aa}$ of SEQ ID NO: 4 is serine (S). In certain embodiments, Xaa$_2$ in the CTP$_{6aa}$ of SEQ ID NO: 4 is glutamine (Q). In certain embodiments, Xaa$_3$ in the CTP$_{6aa}$ of SEQ ID NO: 4 is serine (S). In certain embodiments, Xaa$_4$ in the CTP$_{6aa}$ of SEQ ID NO: 1 is arginine (R). In certain embodiments, Xaa$_1$ and Xaa$_2$ in the CTP$_{6aa}$ of SEQ ID NO: 4 are serine (S) and glutamine (Q), respectively. In certain embodiments, Xaa$_1$ and Xaa$_3$ in the CTP$_{6aa}$ of SEQ ID NO: 4 are both serine (S). In certain embodiments, Xaa$_1$ and Xaa$_4$ in the CTP$_{6aa}$ of SEQ ID NO: 4 are serine (S) and arginine (R), respectively. In certain embodiments, Xaa$_2$ and Xaa$_3$ in the CTP$_{6aa}$ of SEQ ID NO: 4 are glutamine (Q) and serine (S), respectively. In certain embodiments, the CTP$_{6aa}$ comprises the sequence SQYSRT (SEQ ID NO: 5).

In one aspect the invention is based, in part, upon the discovery of a six amino acid Cardiac-specific Targeting-Peptide (CTP$_{6aa}$) comprising the sequence of S Q Xaa$_1$ S R Xaa$_2$ (SEQ ID NO: 6). In certain embodiments, Xaa$_1$ in the CTP$_{6aa}$ of SEQ ID NO: 6 is alanine (A) and the CTP$_{6aa}$ comprises the sequence of SQASRXaa$_2$ (SEQ ID NO: 7), or optionally, Xaa$_1$ in the CTP$_{6aa}$ of SEQ ID NO: 6 is tryptophan (W) and the CTP$_{6aa}$ comprises the sequence of SQWSRXaa$_2$ (SEQ ID NO: 8), or Xaa$_1$ in the CTP$_{6aa}$ of SEQ ID NO: 6 is tyrosine (Y) and the CTP$_{6aa}$ comprises the sequence of SQYSRXaa$_2$ (SEQ ID NO: 8). In certain embodiments, Xaa$_2$ in the CTP$_{6aa}$ of SEQ ID NO: 6 is threonine (T), and Xaa$_1$ in the CTP$_{6aa}$ of SEQ ID NO: 6 is alanine (A), tryptophan (W), or tyrosine (Y) comprising the sequence of SQASRT (SEQ ID NO: 10), SQWSRT (SEQ ID NO: 11), or SQYSRT (SEQ ID NO: 5), respectively. In certain embodiments, Xaa$_2$ in the CTP$_{6aa}$ of SEQ ID NO: 6 is alanine (A). In certain embodiments, Xaa$_1$ in the CTP$_{6aa}$ of SEQ ID NO: 6 is tyrosine (Y) and Xaa$_2$ is alanine (A). In certain embodiments, the CTP$_{6aa}$ comprises the sequence SQYSRT (SEQ ID NO: 5).

In certain embodiments, the CTP$_{6aa}$ of SEQ ID NO: 4 and SEQ ID NO: 6, for example SEQ ID NO: 5, is a recombinant or synthetically prepared peptide.

In one aspect, CTP$_{6aa}$ of SEQ ID NO: 4, 6, 7, 8, 5, 9, 10, or 11 is conjugated to a nanoparticle. In certain embodiments the CTP$_{6aa}$ of SEQ ID NO: 5 is conjugated to a nanoparticle.

In certain non-limiting embodiments the CTP$_{6aa}$ has a net charge of between about +0.8 to +1.2 at pH=7. In certain non-limiting embodiments the CTP$_{6aa}$ peptide has a net charge of about 1.1 at pH=7.

In certain non-limiting embodiments, the CTP$_{6aa}$ has an isoelectric point at between pH 8 and pH 9. In certain non-limiting embodiments, the CTP$_{6aa}$ peptide has an isoelectric point at pH 8.56.

In certain non-limiting embodiments, the CTP$_{6aa}$ has an average hydrophilicity index of between −0.2 and −0.6. In certain non-limiting embodiments, the CTP$_{6aa}$ peptide has an average hydrophilicity index of −0.4.

In certain non-limiting embodiments, the CTP of any one of SEQ ID NOs: 1-35 is comprised of (L) amino acids.

In certain non-limiting embodiments, the CTP of any one of SEQ ID NOs: 1-35 is comprised of (D) amino acids.

In certain embodiments, any of the foregoing CTP peptides of any one of SEQ ID NOs: 1-35 may be isolated. For example, in certain embodiments, the $CTP_{6aa}$ of SEQ ID NO: 1, 2, or 5 is isolated.

In another aspect, the invention provides $CTP_{6aa}$ comprising at least one (for example, one or two) mutation(s) at a position corresponding to wild type $CTP_{6aa}$ of SEQ ID NO: 5, wherein the at least one mutation is present at position 3 or 6. In certain embodiments, the mutation may be a conservative substitution relative to wild type $CTP_{6aa}$ of SEQ ID NO: 5, whereas in certain other embodiments, the mutation may be non-conservative substitutions relative to wild type $CTP_{6aa}$ of SEQ ID NO: 5.

As used herein, the term "conservative substitution" refers to a substitution with a structurally similar amino acid. Non conservative substitutions are amino acid substitutions that are not conservative substitutions.

As disclosed herein, a $CTP_{6aa}$ of any one of SEQ ID NOs: 5-9, for example SEQ ID NO: 5, has higher transducing/penetrating activity than that of SEQ ID NO: 1 or 24. For example, a $CTP_{6aa}$ of SEQ ID NO: 5 or 6 may have from 2-50 fold higher transducing activity than that of SEQ ID NO: 1 or 24. In certain embodiments, the $CTP_{6aa}$ of any one of SEQ ID NOs: 5-9, for example SEQ ID NO: 5, has from about 2 to about 50, from about 2 to about 40, from about 2 to about 30, from about 2 to about 20, from about 2 to about 10, from about 2 to about 5, from about 5 to about 50, from about 5 to about 40, from about 5 to about 30, from about 5 to about 20, from about 5 to about 10, from about 10 to about 50, from about 10 to about 40, from about 10 to about 30, from about 10 to about 20, from about 20 to about 50, from about 20 to about 40, from about 20 to about 30, from about 30 to about 50, from about 30 to about 40, from about 40 to about 50, about 2, about 5, about 10, about 20, about 30, about 40, or about 50 fold higher transducing activity than that of SEQ ID NO: 1 or 2.

It is contemplated that a disclosed CTP of any one of SEQ ID NOs: 1-35, for example SEQ ID NO: 1, 2, or 5, may be modified, engineered or chemically conjugated. For example, it is contemplated that a disclosed CTP of any one of SEQ ID NOs: 1-35, for example SEQ ID NO: 1, 2, or 5, can be conjugated to an effector agent using standard in vitro conjugation chemistries. If the effector agent is another polypeptide, the CTP of any one of SEQ ID NOs: 1-35, for example SEQ ID NO: 1, 2, or 5, can be chemically conjugated to the effector or joined to the effector as a fusion protein. Construction of fusion proteins is within ordinary skill in the art.

In certain embodiments, depending upon a particular mode of administration or site of activity, a disclosed CTP of any one of SEQ ID NOs: 1-35, for example SEQ ID NO: 1, 2, or 5, can be modified with a moiety that improves its stabilization and/or retention in circulation, e.g., in blood, serum, or other tissues. For example, a disclosed CTP of any one of SEQ ID NOs: 1-35, for example SEQ ID NO: 1, 2, or 5, may be conjugated to a polymer, e.g., a substantially non-antigenic polymer, such as a polyalkylene oxide or a polyethylene oxide. In certain embodiments, a disclosed CTP of any one of SEQ ID NOs: 1-35, for example SEQ ID NO: 1, 2, or 5, is conjugated to a water-soluble polymer, e.g., a hydrophilic polyvinyl polymer, e.g., polyvinylalcohol or polyvinylpyrrolidone. Examples of such polymers include polyalkylene oxide homopolymers such as polyethylene glycol (PEG) or polypropylene glycols, polyoxyethylenated polyols, copolymers thereof and block copolymers thereof.

Additional useful polymers include polyoxyalkylenes such as polyoxyethylene, polyoxypropylene, and block copolymers of polyoxyethylene and polyoxypropylene, polymethacrylates, carbomers, and branched or unbranched polysaccharides.

In another aspect, the $CTP_{6aa}$ of SEQ ID NO: 4, 6, 7, 8, 5, 9, 10, or 11 is conjugated to a detectable agent. In certain embodiments, the $CTP_{6aa}$ of SEQ ID NO: 5 is conjugated to a detectable agent. In certain embodiments, the $CTP_{6aa}$ of SEQ ID NO: 4, 6, 7, 8, 5, 9, 10, or 11 is conjugated to a detectable agent via an ester linkage.

In certain embodiments, the $CTP_{6aa}$ of SEQ ID NO: 4, 6, 7, 8, 5, 9, 10, or 11 is conjugated to a radionuclide or radioactive moiety, biotin, luciferase, an enzyme, rhodamine, a fluorophore, nanoparticle, microbubbles, liposomes or a luminescent moiety. In certain embodiments, the $CTP_{6aa}$ of SEQ ID NO: 5 is conjugated to a radionuclide or radioactive moiety, biotin, luciferase, an enzyme, rhodamine, a fluorophore, nanoparticle, microbubbles, liposomes or a luminescent moiety. In certain embodiments, the $CTP_{6aa}$ of SEQ ID NO: 4, 6, 7, 8, 5, 9, 10, or 11 is conjugated to a radionuclide or radioactive moiety, biotin, luciferase, an enzyme, rhodamine, a fluorophore, nanoparticle, microbubbles, liposomes or a luminescent moiety, via an ester linkage.

In another aspect, the present disclosure provides a method of imaging or detecting a tissue, comprising administering an effective amount of a composition comprising the detectable agent-conjugated $CTP_{6aa}$ of SEQ ID NO: 4, 6, 7, 8, 5, 9, 10, or 11 to a subject; exposing the subject to conditions conducive to detection of the $CTP_{6aa}$ conjugate; and obtaining an image. In certain embodiments, the detectable agent-conjugated $CTP_{6aa}$ of SEQ ID NO: 5 is used in a method of imaging or detecting a tissue.

In another aspect, the present disclosure provides a $CTP_{6aa}$ of SEQ ID NO: 4, 6, 7, 8, 5, 9, 10, or 11 formulated as a delivery vehicle/agent. In certain embodiments, the $CTP_{6aa}$ of SEQ ID NO: 4, 6, 7, 8, 5, 9, 10, or 11 is conjugated to a drug or therapeutic, a nanoparticle, a peptide, a protein, or a detectable agent. In certain embodiments, the $CTP_{6aa}$ of SEQ ID NO: 4, 6, 7, 8, 5, 9, 10, or 11 is conjugated to a drug or therapeutic, a nanoparticle, a peptide, a protein, or a detectable agent via an ester linkage. In certain embodiments, the $CTP_{6aa}$ of SEQ ID NO: 5 is formulated as a delivery vehicle/agent.

In certain embodiments, the $CTP_{6aa}$ of SEQ ID NO: 4, 6, 7, 8, 5, 9, 10, or 11 is linked/conjugated to the drug or therapeutic, the nanoparticle, the peptide, the protein, or the detectable agent via an ester linkage, disulfide or protease sensitive linkers. In certain embodiments, the $CTP_{6aa}$ of SEQ ID NO: 5 is linked/conjugated to the drug or therapeutic, the nanoparticle, the peptide, the protein, or the detectable agent via an ester linkage, disulfide, or protease sensitive linkers.

In certain embodiments, the nanoparticle conjugated to the $CTP_{6aa}$ of SEQ ID NO: 4, 6, 7, 8, 5, 9, 10, or 11 comprises a drug or therapeutic agent selected from an antibody or fragment thereof, SB239063, superoxide dismutase, HGF, FGF-1, FGF-2, an NF-κB inhibitor, NSD peptide, heme oxygenase, an antioxidant, iNOS, S100A1, catalase, glutathione peroxidase, a TGFβ inhibitor, VEGF, sonic hedgehog protein, HGF, an IAP, prostaglandin, Pyrvinium Pamoate, and Diprotin A, Szeto-Schiller peptide, cyclosporine, amiodarone.

In another aspect, the present disclosure provides a method of treating cardiac tissue or a cardiac condition in a subject in need thereof, comprising administering to the subject a therapeutically effective amount of a composition comprising the $CTP_{6aa}$ of SEQ ID NO: 4, 6, 7, 8, 5, 9, 10, or 11. In certain embodiments, the $CTP_{6aa}$ of SEQ ID NO: 5 is used in a method of treating cardiac tissue or a cardiac condition in a subject in need thereof.

In another aspect, the present disclosure provides a method of introducing a cargo into a cardiac muscle cell comprising administering, to the cardiac muscle cell, an amount of a complex comprising the $CTP_{6aa}$ of SEQ ID NO: 4, 6, 7, 8, 5, 9, 10, or 11 linked to a cargo effective to introduce the cargo into the muscle cell. In certain embodiments, the cargo comprises a radioisotope, fluorescent marker, gadolinium marker, luciferase marker, microsphere or nanoparticle. In certain embodiments, the $CTP_{6aa}$ of SEQ ID NO: 5 is used in a method of introducing a cargo into a cardiac muscle cell. In certain embodiments, the $CTP_{6aa}$ of SEQ ID NO: 4, 6, 7, 8, 5, 9, 10, or 11 is conjugated to the cargo via an ester linkage.

In another aspect, the present disclosure provides a method of treating a human subject suffering from a myocardial infarction, comprising introducing a cargo into a cardiac muscle cell of the human subject comprising administering, to the human subject, a therapeutically effective amount of a complex comprising the $CTP_{6aa}$ of SEQ ID NO: 4, 6, 7, 8, 5, 9, 10, or 11 linked to a cargo, where the cargo inhibits cell death, inhibits arrhythmias, improves contractility, lengthens subject survival, or a combination thereof. In certain embodiment, the cargo is selected from an NF-κB inhibitor, NSD peptide, heme oxygenase, an antioxidant, iNOS, S100A1, superoxide dismutase, catalase, glutathione peroxidase, a TGFβ inhibitor, VEGF, FGF-1, FGF-2, sonic hedgehog protein, HGF and an IAP. In certain embodiments, the $CTP_{6aa}$ of SEQ ID NO: 5 is used in a method of treating a human subject suffering from a myocardial infarction. In certain embodiments, the $CTP_{6aa}$ of SEQ ID NO: 4, 6, 7, 8, 5, 9, 10, or 11 is conjugated to the cargo via an ester linkage.

In another aspect, the present disclosure provides a method of treating a human subject suffering from a myocardial infarction, comprising introducing a cargo into a cardiac muscle cell of the human subject comprising administering, to the human subject, a therapeutically effective amount of a complex comprising the $CTP_{6aa}$ of SEQ ID NO: 4, 6, 7, 8, 5, 9, 10, or 11 linked to a cargo, wherein the cargo inhibits cell death, inhibits arrhythmias, improves contractility, lengthens subject survival, or a combination thereof. In certain embodiments, the cargo is selected from an NF-κB inhibitor, NBD peptide, heme oxygenase, an antioxidant, iNOS, S100A1, superoxide dismutase, catalase, glutathione peroxidase, a TGFβ inhibitor, VEGF, FGF-1, FGF-2, sonic hedgehog protein, HGF and an IAP. In certain embodiments, the $CTP_{6aa}$ of SEQ ID NO: 4, 6, 7, 8, 5, 9, 10, or 11 is linked/conjugated to the cargo via an ester linkage.

In another aspect, the present disclosure provides a method of treating a subject suffering from a metabolic defect that damages the heart comprising introducing a cargo into a cardiac muscle cell of the human subject comprising administering, to the subject, a therapeutically effective amount of a complex comprising the $CTP_{6aa}$ of SEQ ID NO: 4, 6, 7, 8, 5, 9, 10, or 11 linked to a cargo, wherein the cargo corrects the metabolic defect. In certain embodiments, the metabolic defect is Gaucher's disease and the cargo is glucocerebrosidase. In certain embodiments, the $CTP_{6aa}$ of SEQ ID NO: 5 is used in a method of treating a subject suffering from a metabolic defect that damages the heart. In certain embodiments, the $CTP_{6aa}$ of SEQ ID NO: 4, 6, 7, 8, 5, 9, 10, or 11 is linked/conjugated to the cargo via an ester linkage.

In another aspect, the present disclosure provides a method of treating a subject suffering from a metabolic defect that damages the heart comprising introducing a cargo into a cardiac muscle cell of the human subject comprising administering, to the subject, a therapeutically effective amount of a complex comprising the $CTP_{6aa}$ of SEQ ID NO: 4, 6, 7, 8, 5, 9, 10, or 11 linked to a cargo, where the cargo corrects the metabolic defect. In certain embodiments, the metabolic defect is Gaucher's disease and the cargo is glucocerebrosidase. In certain embodiments, the $CTP_{6aa}$ of SEQ ID NO: 5 is used in a method of treating a subject suffering from a metabolic defect that damages the heart. In certain embodiments, the $CTP_{6aa}$ of SEQ ID NO: 4, 6, 7, 8, 5, 9, 10, or 11 is linked/conjugated to the cargo via an ester linkage.

In another aspect, the present disclosure provides a method of introducing a detectable cargo into a cardiac muscle cell comprising administering, to the cardiac muscle cell, an amount of a complex comprising the $CTP_{6aa}$ of SEQ ID NO: 4, 6, 7, 8, 5, 9, 10, or 11 linked to a cargo effective to introduce the cargo into the muscle cell, wherein the cargo comprises a detectable compound. In certain embodiments, the detectable compound comprises a detectable radioisotope, fluorescent marker, gadolinium marker, or luciferase marker. In certain embodiments, the $CTP_{6aa}$ of SEQ ID NO: 5 is used in a method of introducing a detectable cargo into a cardiac muscle cell. In certain embodiments, the $CTP_{6aa}$ of SEQ ID NO: 4, 6, 7, 8, 5, 9, 10, or 11 is linked/conjugated to the cargo via an ester linkage.

In another aspect, the present disclosure provides a method of introducing a detectable cargo into a cardiac muscle cell comprising administering, to the cardiac muscle cell, an amount of a complex comprising the $CTP_{6aa}$ of SEQ ID NO: 4, 6, 7, 8, 5, 9, 10, or 11 linked to a cargo effective to introduce the cargo into the muscle cell, wherein the cargo comprises a detectable compound. In certain embodiments, the detectable compound comprises a detectable radioisotope, fluorescent marker, gadolinium marker, or luciferase marker. In certain embodiments, the $CTP_{6aa}$ of SEQ ID NO: 5 is used in a method of introducing a detectable cargo into a cardiac muscle cell. In certain embodiments, the $CTP_{6aa}$ of SEQ ID NO: 4, 6, 7, 8, 5, 9, 10, or 11 is conjugated to the cargo via an ester linkage.

In another aspect, the invention provides a $CTP_{6aa}$ of any one of SEQ ID NOs: 5-9, for example SEQ ID NO: 5, having a higher level of cardiac transduction compared to the transduction of a peptide of SEQ ID NO: 1 or SEQ ID NO: 24, for example, under the conditions set forth in Example 1.

It is contemplated that any of the foregoing $CTP_{6aa}$ peptides of SEQ ID NOs: 4-11 may, for example, have 5-20 fold higher transducing capacity, compared to a peptide of SEQ ID NO: 1 or SEQ ID NO: 24.

II. Cargo

According to the invention, the CTP of any one of SEQ ID NOs: 1-35, for example SEQ ID NO: 5, is linked with a cargo molecule to form a complex, optionally via a linker molecule or molecules. The cargo molecule may be a protein (including a glycoprotein), a nucleic acid, a carbohydrate, a lipid, or a combination thereof. In some embodiments, the cargo molecule is an active pharmaceutical ingredient, for example, an active pharmaceutical ingredient with antiarrhythmic properties. For example, in some embodiments described herein, a cargo molecule is a class I antiarrhythmic compound (for example, a subclass a compound, a subclass b compound, or a subclass c compound), a class II antiarrhythmic compound, a class III antiarrhythmic compound, a class IV antiarrhythmic compound, a sodium channel blocker, an anticholinergic compound, quinidine, ajmaline, hydroquinidine, lorajmine, prajmaline, sparteine, procainamide, disopyramide, lidocaine, a lidocaine analog, phenytoin, tocainide, mexiletine, flecainide, indecainide, lorcainide, encainide, ethacizine, propafenone, moracizine, a betablocker, carteolol, carvedilol, labetalol, nadolol, penbutolol, pindolol, propranolol, sotalol, timolol, acebutolol, atenolol, betaxolol, bisoprolol, esmolol, metoprolol, nebivolol, a potassium channel blocker, amiodarone, dronedarone, E-4031, vemakalant, nifekalant, bretylium, bunaftine, celivarone, sotalol, ibutilide, dofetilide, tedisamil, a calcium channel blocker, a dihydropyridine calcium channel blocker, a non-dihydropyridine calcium channel blocker, amlodipine, felodipine, isradipine, nicardipine, nifedipine, nimodipine, nitrendipine, verapamil, diltiazem, adenosine, a benzodiazepine, a barbiturate, a muscarinic antagonist, a muscarinic agonist, digoxin, digitoxin, ouabain, magnesium sulfate, or atropine.

In certain non-limiting embodiments, the cargo is a protein. In certain non-limiting embodiments, the protein is selected from the group consisting of a cytokine, a growth factor, an enzyme, an ion channel, and an anti-inflammatory protein.

In certain non-limiting embodiments, the cargo is an antioxidant.

In certain non-limiting embodiments, the cargo is a nucleic acid. Non-limiting examples of such nucleic acid include DNA, RNA, antisense RNA, interfering RNA, microRNA, catalytic RNA, and catalytic DNA.

The present disclosure provides Cardiac Targeting Peptides ("CTP") linked/conjugated to Neuregulin-1β-CTP or a moiety having antiarrhythmic properties, for example amiodarone. In certain non-limiting embodiments, the N-terminus of a $CTP_{12aa}$ comprising the sequence of APWHLSSQYSRT (SEQ ID NO: 1), a $CTP_{6aa}$ having a sequence of SQYSRT (SEQ ID NO: 5), or a $CTP_{12aa}$ having a sequence of AAWHLSSQYSRT (SEQ ID NO: 2 (CTP-P2A)) is linked/conjugated to Neuregulin-1β-CTP or a moiety having antiarrhythmic properties, for example amiodarone. In certain embodiments, the CTP is linked/conjugated to a second moiety having antiarrhythmic properties, for example amiodarone.

In certain non-limiting embodiments, the CTP linked to a therapeutic moiety specifically targets cardiac tissue. "Specifically targets cardiac tissue" means that when said CTP conjugate, linked to a second peptide sequence, a protein, or a small molecule to form a conjugated protein, is injected into a mammal, the conjugated protein is transduced into cardiac tissue at much higher levels than it is transduced into other tissues, such as, for example, liver, kidney, lung, skeletal muscle, or brain.

In certain non-limiting embodiments, the CTP (e.g., $CTP_{6aa}$ of SEQ ID NO: 5) has an average hydrophilicity index of between −0.2 and −0.6. In certain non-limiting embodiments, the CTP (e.g., CTP of SEQ ID NO: 5) has an average hydrophilicity index of −0.4.

In certain non-limiting embodiments, the CTP of SEQ NO: 1, 2, 3, 4, or 5 is comprised of (L) amino acids. In certain non-limiting embodiments, the CTP of SEQ ID NO: 1, 2, 3, 4, or 5 is comprised of (D) amino acids.

The present disclosure is based, in part, on directly delivering Neuregulin-1β or a moiety having antiarrhythmic properties, for example amiodarone, to the heart using CTP to target peptide delivery to cells of the heart, for example, cardiomyocytes. For example, in some embodiments the invention provides a method of delivering Neuregulin-1β or a moiety having antiarrhythmic properties, for example, amiodarone, to cells of a subject's heart, for example, a subject's cardiomyocytes. In some embodiments, the subject is a mammal, for example, a primate, for example a human. Thus, in some embodiments the invention provides a method of delivering Neuregulin-1β or a moiety having antiarrhythmic properties, for example, amiodarone, to cells of a human subject's heart, for example, a human subject's cardiomyocytes. In some embodiments the invention provides a method of delivering Neuregulin-1β or a moiety having antiarrhythmic properties, for example, amiodarone, to cells of a subject's heart, for example, a subject's cardiomyocytes, by administering a peptide that includes CTP conjugated to antiarrhythmics, for example, by Schiff base chemistry, to the subject. In some embodiments, the peptide can be introduced by means of a cell or a virus that includes a nucleic acid encoding a CTP sequence.

In certain embodiments, the invention provides formulating a peptide composition, for example, an antiarrhythmic moiety-CTP composition or Neuregulin-1β-CTP composition, in a stable formulation for delivery to cells in vitro as well as to animals via intravenous perfusion. In certain embodiments, the invention provides delivering the formulated composition to a mammalian cardiomyoblast cell and monitoring for cellular toxicity by performing a cell viability assay. In certain embodiments, the invention provides delivering a peptide, for example, an antiarrhythmic moiety-CTP or Neuregulin-1β-CTP, to a mammalian cardiomyoblast cell line. In certain embodiments, the invention provides delivering an antiarrhythmic moiety-CTP to a mammal having arrhythmias, for example atrial and/or ventricular fibrillation. In some embodiments, the invention also includes observing one or more echocardiographic parameters, for example, left ventricular wall thickness, left ventricular function, and/or mitral in-flow patterns, to assess diastolic relaxation at various time points before, during, and/or after delivery and/or treatment. In certain embodiments, the invention provides administering an antiarrhythmic moiety-CTP or Neuregulin-1β-CTP intravenously weekly, for example, for 6-12 weeks, and assessing for hepatic, renal, CNS, and/or cardiac toxicity using blood chemistry and/or histology.

In certain embodiments, the invention provides formulating a peptide composition that includes CTP linked/conjugated to a second moiety having an antiarrhythmic property, in a stable formulation for delivery to cells in vitro as well as to animals via intravenous perfusion. In certain embodiments, the invention provides delivering the formulated composition to a mammalian cardiomyoblast cell and monitoring for cellular toxicity by performing a cell viability assay. In certain embodiments, the invention provides delivering a peptide that includes CTP linked/conjugated to a second moiety having an antiarrhythmic property, to a mammalian cardiomyoblast cell line. In certain embodiments, the disclosure provides a method of administering a peptide that includes CTP linked/conjugated to a second moiety having antiarrhythmic properties, where the administering is performed intravenously on a weekly basis for a designated period of time, for example, for 6-12 weeks. In some embodiments, the method further includes assessing for hepatic, renal, CNS, and/or cardiac toxicity using blood chemistry and/or histology.

In another aspect the present disclosure also provides sustained release formulations (long-lasting formulation) suitable for injection to deliver a peptide comprising Cardiac-specific Targeting-Peptide (CTP) linked/conjugated to Neuregulin-1β or a moiety having antiarrhythmic properties.

In another aspect, the present disclosure provides a method of imaging or detecting a heart tissue (e.g., a human heart tissue), by administering a peptide that includes CTP linked/conjugated to a moiety having an antiarrhythmic property to a subject; exposing the subject to conditions conducive to detection of the peptide; and obtaining an image.

In embodiments, the invention provides a peptide that includes a twelve amino acid Cardiac-specific Targeting-Peptide (CTP$_{12aa}$) comprising the sequence of Ala-Pro-Trp-His-Leu-Ser-Ser-Gln-Tyr-Ser-Arg-Thr (SEQ ID NO: 1) linked/conjugated to a second peptide sequence, a protein, or a small molecule that has reactive oxygen species (ROS) scavenging properties. In some embodiments, the second peptide sequence, protein, or small molecule is conjugated upstream of the N-terminus of the CTP peptide. In some embodiments the peptide can include an ester linkage between the CTP and the second peptide sequence, protein, or small molecule, and the ester linkage can only be cleaved by an intracellular esterase. Examples of peptide sequences, proteins, and small molecules with ROS scavenging properties include, but are not limited to, heme-oxygenase 1, resveratrol, N-acetyl-cysteine, N-tert-butyl-α-phenylni-trone, and 4-hydroxy-2,2,6,6-tetramethylpiperidine-1-oxyl.

In some embodiments, the peptide is optionally further labelled at both the C- and N-termini. For example, in some embodiments, the peptide is labelled with a green fluores-cent moiety, for example, 6-carboxyfluorescein, and a red fluorescent moiety, for example, Cy5.5. For example, in some embodiments, the peptide is labelled with a green fluorescent moiety at its N-terminus and a red fluorescent moiety at its C-terminus. In some embodiments, the peptide is labelled with a red fluorescent moiety at its N-terminus and a green fluorescent moiety at its C-terminus.

The present disclosure is based, in part, on directly delivering an ROS scavenging peptide (for example, SS-31 or SS-02), protein, or small molecule to the heart using CTP to target peptide delivery to cells of the heart, for example, cardiomyocytes. ROS scavenging peptides include Szeto-Schiller (SS) peptides (for example, SS-01, SS-02, and SS-31), which contain alternating aromatic and basic amino acids, including tyrosine or dimethyltyrosine, and which are highly cell permeable. SS peptides are described in Szeto HH, (2006) "Cell-permeable, Mitochondrial-targeted, Pep-tide Antioxidants" *The AAPS Journal* 8(2):E277-E283, the entire contents of which are incorporated herein by refer-ence. In some embodiments the invention provides a method of delivering an ROS scavenging peptide (for example, SS-31 or SS-02), protein, or small molecule to cells of a subject's heart, for example, a subject's cardiomyocytes. In some embodiments, the subject is a mammal, for example, a primate, for example, a human. Thus, in some embodi-ments the invention provides a method of delivering an ROS scavenging peptide (for example, SS-31 or SS-02), protein, or small molecule to cells of a human subject's heart, for example, a human subject's cardiomyocytes. In some embodiments the invention provides a method of delivering an ROS scavenging peptide (for example, SS-31 or SS-02), protein, or small molecule to cells of a subject's heart, for example, a subject's cardiomyocytes, by administering a peptide that includes CTP linked/conjugated to an ROS scavenging peptide (for example, SS-31 or SS-02), protein, or small molecule, for example, by an ester linkage, to the subject. In some embodiments, the peptide can be introduced by means of a cell or a virus that includes a nucleic acid encoding a CTP linked/conjugated peptide sequence.

In some aspects, the invention provides a method of scavenging ROS in cell culture by exposing a cell culture (for example, cells and/or cell culture media) to a peptide that includes CTP linked/conjugated to a second peptide sequence, a protein, or a small molecule with ROS scav-enging properties. For example, in some embodiments, the invention provides a method of scavenging ROS in cell culture by exposing a cell culture to a peptide that includes CTP linked/conjugated to SS-31 (SS-CTP-31) or CTP con-jugated to SS-02 (SS-CTP-02). In some embodiments, exposing a cell culture to a peptide that includes CTP linked/conjugated to a second peptide sequence, a protein, or a small molecule with ROS scavenging properties is achieved by expressing the peptide in one or more cells in the cell culture and/or by viral infection.

In certain embodiments, the invention provides formulat-ing a peptide composition, for example, an SS-CTP com-position, in a stable formulation for delivery to cells in vitro as well as to animals via intravenous perfusion. In certain embodiments, the invention provides delivering the formu-lated composition to a mammalian cardiomyoblast cell and monitoring for cellular toxicity by performing a cell viability assay. In certain embodiments, the invention provides deliv-ering a peptide, for example, an SS-CTP, to a mammalian cardiomyoblast cell line challenged with oxidative stress (for example, a cardiomyoblast cell line challenged with oxidative stress using hydrogen peroxide) as a stressor. In some embodiments, the invention also includes assessing mitochondrial function at baseline, under stress with $H_2O_2$, and in cells treated with an SS-CTP prior to challenge with $H_2O_2$ using a Seahorse analyzer (Agilent Technologies, Inc., Santa Clara, CA, USA). In certain embodiments, the inven-tion provides delivering an SS-CTP to a mammal having diastolic heart failure (DHF). In some embodiments, the invention also includes observing one or more echocardio-graphic parameters, for example, left ventricular wall thick-ness, left ventricular function, and/or mitral in-flow patterns, to assess diastolic relaxation at various time points before, during, and/or after delivery and/or treatment. In certain embodiments, the invention provides administering an SS-CTP intravenously weekly, for example, for 6-12 weeks, and assessing for hepatic, renal, CNS, and/or cardiac toxicity using blood chemistry and/or histology.

In certain embodiments, the invention provides formulat-ing a peptide composition that includes CTP linked/conju-gated to a second peptide sequence, a protein, or a small molecule with ROS scavenging properties, in a stable for-mulation for delivery to cells in vitro as well as to animals via intravenous perfusion. In certain embodiments, the invention provides delivering the formulated composition to a mammalian cardiomyoblast cell and monitoring for cel-lular toxicity by performing a cell viability assay. In certain embodiments, the invention provides delivering a peptide that includes CTP linked/conjugated to a second peptide sequence, a protein, or a small molecule with ROS scav-enging properties, to a mammalian cardiomyoblast cell line challenged with oxidative stress (for example, a cardiomyo-blast cell line challenged with oxidative stress using hydro-gen peroxide) as a stressor. In some embodiments, the invention also includes assessing mitochondrial function at baseline, under stress with $H_2O_2$, and in cells treated with the peptide prior to challenge with $H_2O_2$, using Seahorse. In certain embodiments, the invention provides delivering a peptide that includes CTP linked/conjugated to a second peptide sequence, a protein, or a small molecule with ROS scavenging properties to a mammal having diastolic heart failure (DHF). In some embodiments, the invention also includes observing one or more echocardiographic parameters, for example, left ventricular wall thickness, left ventricular function, and/or mitral in-flow patterns, to assess diastolic relaxation at various time points before, during, and/or after delivery and/or treatment. In certain embodiments, the invention provides administering a peptide that includes CTP linked/conjugated to a second peptide sequence, a protein, or a small molecule with ROS scavenging properties intravenously weekly, for example, for 6-12 weeks, and assessing for hepatic, renal, CNS, and/or cardiac toxicity using blood chemistry and/or histology.

In another aspect, the present disclosure provides a method of imaging or detecting a heart tissue (e.g., a human heart tissue), by administering a peptide that includes CTP linked/conjugated to a second peptide sequence, a protein, or a small molecule with ROS scavenging properties (for example, an SS-CTP conjugate) to a subject; exposing the subject to conditions conducive to detection of the peptide, and obtaining an image.

In certain embodiments, the $CTP_{6aa}$ of SEQ ID NO: 4, 6, 7, 8, 5, 9, 10, or 11 is linked/conjugated or fused to a tafazzin peptide. In certain embodiments, the $CTP_{6aa}$ of SEQ ID NO: 4, 6, 7, 8, 5, 9, 10, or 11 is linked/conjugated or fused to the tafazzin peptide through a polypeptide linker. In certain embodiments, the $CTP_{6aa}$ of SEQ ID NO: 5 is conjugated or fused to a tafazzin peptide.

In certain embodiments, one specific non-limiting example of a cargo is a NF-κB inhibitor, for example NBD peptide TALDWSWLQTE (SEQ ID NO:35). One specific non-limiting example of a cargo is heme oxygenase, for example human heme oxygenase. One specific non-limiting example of a cargo is inducible nitric oxide synthase ("iNOS"), for example human iNOS.

In certain embodiments, one specific non-limiting example of a cargo is S100A1 (an inotropic regulator of myocardial contractility. One specific non-limiting example of a cargo is extracellular superoxide dismutase. Further specific non-limiting examples of cargo include Cu/Zn-SOD, Mn-SOD, catalase, and glutathione peroxidase. One specific non-limiting example of cargo is transforming growth factor beta ("TGFβ") type II receptor (Ad.CAG-s TGFβII), a competitive inhibitor of TGFβ. One specific non-limiting example of cargo is VEGF (vascular endothelial growth factor), for example human VEGF. One specific non-limiting example of cargo is fibroblast growth factor (FGF), for example human FGF-1 or FGF-2. One specific non-limiting example of cargo is hepatocyte growth factor ("HGF"). One set of non-limiting examples of cargo is an apoptosis inhibitor, such as one of the so-called inhibitors of apoptosis ("IAPs"), for example, the human IAPs c-IAP1, c-IAP2, and XIAP. One specific non-limiting example of cargo is Sonic Hedgehog protein. One specific non-limiting example of cargo is glucocerebrosidase, for example human glucocerebrosidase used for treatment in Gaucher's disease. One specific non-limiting example of cargo is an RNAi that inhibits expression of TGFβ.

In another set of non-limiting embodiments, the cargo is a nanoparticle or a microsphere containing a diagnostic or therapeutic agent. In another set of non-limiting embodiments, the cargo is a vector comprising a therapeutic gene, for example an adenovirus vector or a lentivirus vector. In another set of non-limiting embodiments, the cargo is a detectable compound for analysis of uptake in viable cardiac cells versus non-viable cells following ischemic injury. Non-limiting examples of detectable compounds include fluorodeoxyglucose, a technetium-99 or other radioisotope-labelled cargo, fluorescent markers, gadolinium markers, etc. One non-limiting example of a radioisotope-labelled cargo is Sestamibi, a coordination complex of the radioisotope technetium-99m with the ligand methoxyisobutylisonitrile ("MIBI").

III. Linkers

The CTP of any one of SEQ ID NOs: 1-35, for example SEQ ID NO: 1, 2, or 5, and the cargo are linked covalently or non-covalently, optionally via one or more linker molecules. Where the bond is a covalent bond, CTP of any one of SEQ ID NOs: 1-35 and cargo, optionally with a linker(s) between, may be joined via one or more peptide bond, thioester bond, thioether bond, carbamate bond, etc., which can be created according to methods generally and well known in the art.

In certain embodiments, the linker may comprise a cleavage site that may, upon enzymatic or chemical cleavage, release the CTP of any one of SEQ ID NOs: 1-35, for example SEQ ID NO: 5, from its cargo. In certain non-limiting embodiments, the linker may be a ligand pair. As one specific example, the linker may be an avidin/biotin pair.

Accordingly, the invention provides for a complex comprising a CTP of any one of SEQ ID NOs: 1-35, for example SEQ ID NO: 1, 2, or 5, linked to a cargo. The complex may comprise additional elements. For example, the CTP of any one of SEQ ID NOs: 1-35, for example SEQ ID NO: 1, 2, or 5, and/or cargo may be conjugated to one or more additional molecule that improves delivery or stability. As one non-limiting example, the CTP of any one of SEQ ID NOs: 1-35, for example SEQ ID NO: 1, 2, or 5, and/or cargo may be PEGylated. As another non-limiting example, the cargo may be linked to a nuclear transport peptide. As another non-limiting example, the cargo may be linked to a detectable compound.

IV. Method of Introducing a Cargo

In another aspect, the present disclosure provides a method of introducing a cargo into a cardiac tissue comprising administering, to the cardiac tissue, a complex comprising a CTP of any one of SEQ ID NOs: 1-35, for example SEQ ID NO: 1, 2, or 5, linked to the cargo molecule.

The present disclosure provides for a method of introducing a cargo into a cardiac muscle cell comprising administering, to the cardiac muscle cell, a complex comprising a CTP of any one of SEQ ID NOs: 1-35, for example SEQ ID NO: 1, 2, or 5, linked to the cargo. For example, the present disclosure provides a method of introducing a cargo into a cardiac muscle cell comprising administering, to the cardiac muscle cell, an amount of a complex comprising the CTP of any one of SEQ ID NOs: 1-35, for example SEQ ID NO: 1, 2, or 5, linked to a cargo effective to introduce the cargo into the muscle cell. In certain embodiments, the cargo comprises a radioisotope, fluorescent marker, gadolinium marker, luciferase marker, microsphere or nanoparticle.

The present disclosure provides for a method of selectively delivering a cargo to cardiac tissue in a subject, comprising administering, to the subject, a complex comprising the CTP of any one of SEQ ID NOs: 1-35, for example SEQ ID NO: 1, 2, or 5, linked to the cargo. The present disclosure provides for a method of selectively delivering a cargo to a cardiac muscle cell in a subject, comprising administering, to the subject, a complex comprising a CTP of any one of SEQ ID NOs: 1-35, for example SEQ ID NO: 1, 2, or 5, linked to the cargo.

In another aspect, the present disclosure provides a method of introducing a detectable cargo into a cardiac muscle cell comprising administering, to the cardiac muscle cell, an amount of a complex comprising a CTP of any one of SEQ ID NOs: 1-35, for example SEQ ID NO: 5, linked to a cargo effective to introduce the cargo into the muscle cell, wherein the cargo comprises a detectable compound. In certain embodiments, the detectable compound comprises a detectable radioisotope, fluorescent marker, gadolinium marker, or luciferase marker.

V. Methods of Use

In one aspect, the present disclosure provides a method of treating cardiac tissue or a cardiac condition in a subject in need thereof, comprising administering to the subject a therapeutically effective amount of a composition comprising a CTP of any one of SEQ ID NOs: 1-35, for example SEQ ID NO: 1, 2, or 5, linked to a therapeutic agent for treating a cardiac disease and/or condition.

In certain embodiments, the present disclosure provides a method of introducing a moiety having antiarrhythmic properties into a cardiac muscle cell comprising administering to the cardiac muscle cell a $CTP_{12aa}$ comprising the sequence of APWHLSSQYSRT (SEQ ID NO: 1), a CTP having a sequence of SQYSRT (SEQ ID NO: 5), or a $CTP_{12aa}$ having a sequence of AAWHLSSQYSRT (SEQ ID NO: 2 (CTP-P2A)) conjugated to a moiety having antiarrhythmic properties, for example amiodarone, in an amount effective to introduce the moiety having antiarrhythmic properties into the muscle cell. In certain embodiments, the peptide further comprises a microsphere or nanoparticle.

In certain embodiments, the present disclosure provides a method of treating a human subject suffering from atrial and/or ventricular arrhythmias, comprising introducing a cargo into a cardiac muscle cell of the human subject by administering to the human subject a $CTP_{12aa}$ comprising the sequence of APWHLSSQYSRT (SEQ ID NO: 1), a $CTP_{6aa}$ having a sequence of SQYSRT (SEQ ID NO: 5), or a $CTP_{12aa}$ having a sequence of AAWHLSSQYSRT (SEQ ID NO: 2 (CTP-P2A)) conjugated to a moiety having antiarrhythmic properties, for example amiodarone. In certain embodiments, the present disclosure provides a method of treating ventricular arrhythmias selected from premature ventricular contractions, ventricular tachycardia, and ventricular fibrillation, by administering to the human subject a $CTP_{12aa}$ comprising the sequence of APWHLSSQYSRT (SEQ ID NO: 1), a $CTP_{6aa}$ having a sequence of SQYSRT (SEQ ID NO: 5), or a $CTP_{12aa}$ having a sequence of AAWHLSSQYSRT (SEQ ID NO: 2 (CTP-P2A)) conjugated to a moiety having antiarrhythmic properties, for example amiodarone.

In certain embodiments, the present disclosure provides a method of treating a human subject suffering from SHF, comprising introducing a cargo into a cardiac muscle cell of the human subject by administering to the human subject a $CTP_{12aa}$ comprising the sequence of APWHLSSQYSRT (SEQ ID NO: 1), a $CTP_{6aa}$ n having a sequence of SQYSRT (SEQ ID NO: 5), or a $CTP_{12aa}$ having a sequence of AAWHLSSQYSRT (SEQ ID NO: 2 (CTP-P2A)) conjugated to Neuregulin-1β.

In certain embodiments, the present disclosure provides a method of performing myocardial perfusion analysis of a subject, by administering to the subject a conjugate of the CTP comprising, for example, SEQ ID NO: 1, 2, 4, or 5 (e.g., an antiarrhythmic-CTP or Neuregulin-1β-CTP), and monitoring through Planar or SPECT imaging, delivery of the conjugate to the subject's heart.

In certain embodiments, the present disclosure provides a method of imaging or detecting a heart tissue, by administering to the subject a conjugate of the CTP comprising, for example, SEQ ID NO: 1 (e.g., an antiarrhythmic-CTP or Neuregulin-1β-CTP); exposing the subject to conditions conducive to detection of the CTP conjugate; and obtaining an image. In this aspect, the antiarrhythmic-CTP optionally further comprises detectable moiety. In certain embodiments, the antiarrhythmic-CTP further comprises a detectable moiety.

Where a conjugate of the CTP comprising, for example, SEQ ID NO: 1 (e.g., an antiarrhythmic-CTP or Neuregulin-1β-CTP) is administered to a subject, the subject may be a human subject or a non-human subject, such as a primate, a companion animal (e.g., dog, cat, horse), a laboratory animal (e.g., mouse, rat, rabbit or guinea pig) or a farm animal (cow, goat, etc.).

A conjugate of the CTP comprising, for example, SEQ ID NO: 1, 2, 4, or 5 (e.g., an antiarrhythmic-CTP or Neuregulin-1β-CTP) may be administered by any route including but not limited to intravenous, intraatrial, intraperitoneal, subcutaneous, oral, rectal, etc.

The present disclosure provides for pharmaceutical compositions comprising a CTP comprising, for example, SEQ ID NO: 1, 2, 4, or 5 linked to a therapeutic agent (e.g., an antiarrhythmic-CTP or Neuregulin-1β-CTP), and a suitable pharmaceutical carrier, for example, water or physiologic saline.

The CTP of any one of SEQ ID NOs: 1-35, for example SEQ ID NO: 1, 2, or 5, disclosed herein can be used to treat various diseases or disorders associated with cardiac tissue or muscle in a subject. In certain embodiments, the method comprises orally administering to the subject an effective amount of a disclosed CTP of any one of SEQ ID NOs: 1-35, for example SEQ ID NO: 1, 2, or 5, either alone or in a combination with another therapeutic agent to treat the disease or disorder in the subject.

In certain embodiments, the CTP of any one of SEQ ID NOs: 1-35, for example SEQ ID NO: 1, 2, or 5, is conjugated or fused to a tafazzin peptide. In certain embodiments, the CTP of any one of SEQ ID NOs: 1-35, for example SEQ ID NO: 1, 2, or 5, is conjugated or fused to the tafazzin peptide through a polypeptide linker.

In another aspect, the present disclosure provides a method of treating a subject having a disorder associated with a tafazzin deficiency or a remodeled cardiolipin deficiency, comprising administering to the subject a therapeutically effective amount of a composition comprising the tafazzin-conjugated CTP of any one of SEQ ID NOs: 1-35, for example SEQ ID NO: 1, 2, or 5. In certain embodiments, the tafazzin-conjugated $CTP_{6aa}$ of SEQ ID NO: 5 is used in treating a subject having a disorder associated with a tafazzin-deficiency or a remodeled cardiolipin-deficiency.

In another aspect, the present disclosure provides a method of treating a subject having, or at risk of developing Barth syndrome, comprising administering to the subject a therapeutically effective amount of a composition comprising the tafazzin-conjugated CTP of any one of SEQ ID NOs: 1-35, for example SEQ ID NO: 5.

In certain embodiments, the present disclosure provides a method of treating a subject having, or at risk of developing Barth syndrome, comprising administering to the subject a therapeutically effective amount of a composition comprising the tafazzin-conjugated $CTP_{6aa}$ of SEQ ID NO: 4, 6, 7, 8, 5, 9, 10, or 11. In certain embodiments, the tafazzin-conjugated $CTP_{6aa}$ of SEQ ID NO: 5 is used for treating a subject having, or at risk of developing Barth syndrome.

In one aspect, the present disclosure provides a method of treating cardiac tissue or a cardiac condition in a subject in need thereof, comprising administering to the subject a therapeutically effective amount of a composition comprising the nanoparticle-conjugated CTP of any one of SEQ ID NOs: 1-35 linked to a moiety having antiarrhythmic properties, for example amiodarone. In certain embodiments the CTP of SEQ ID NO: 1, 2, or 5 is used for treating a cardiac tissue or a cardiac condition in a subject in need thereof, comprising administering to the subject a therapeutically effective amount of a composition comprising the nanoparticle-conjugated CTP of SEQ ID NO: 1, 2, or 5 linked to a moiety having antiarrhythmic properties, for example amiodarone.

In another aspect, the present disclosure provides a method of treating a human subject suffering from a myocardial infarction, comprising introducing a cargo into a cardiac muscle cell of the human subject comprising administering, to the human subject, a therapeutically effective amount of a complex comprising the CTP of any one of SEQ ID NOs: 1-35, for example SEQ ID NO: 5, linked to a cargo, where the cargo inhibits cell death, inhibits arrhythmias, improves contractility, lengthens subject survival, or a combination thereof. In certain embodiments, the cargo is selected from an NF-κB inhibitor, NSD peptide, heme oxygenase, an antioxidant, iNOS, S100A1, superoxide dismutase, catalase, glutathione peroxidase, a TGFβ inhibitor, VEGF, FGF-1, FGF-2, sonic hedgehog protein, HGF and an IAP.

In another aspect, the present disclosure provides a method of treating a subject suffering from a metabolic defect that damages the heart comprising introducing a cargo into a cardiac muscle cell of the human subject comprising administering, to the subject, a therapeutically effective amount of a complex comprising the CTP of any one of SEQ ID NOs: 1-35, for example SEQ ID NO: 5, linked to a cargo, wherein the cargo corrects the metabolic defect. In certain embodiments, the metabolic defect is Gaucher's disease and the cargo is glucocerebrosidase.

The present disclosure provides for a method of treating a subject suffering from a myocardial infarction, comprising administering, to the subject, a therapeutically effective amount of a complex comprising a CTP of any one of SEQ ID NOs: 1-35, for example SEQ ID NO: 5, linked to the cargo, where the cargo (meaning the biological function of the cargo) inhibits cell death, inhibits arrhythmias, improves contractility, lengthens subject survival, or a combination thereof.

The present disclosure provides for a method of treating a subject suffering from angina, comprising administering, to the subject, a therapeutically effective amount of a complex comprising a CTP of any one of SEQ ID NOs: 1-35, for example SEQ ID NO: 5, linked to a cargo, where the cargo reduces the risk of myocardial infarction, inhibits cell death, limits arrhythmias, improves contractility, lengthens subject survival, or a combination thereof.

Non-limiting examples of cargo that may be used to treat myocardial infarction and/or angina include an NF-κB inhibitor, NBD peptide, heme oxygenase, an antioxidant, iNOS, S100A1, superoxide dismutase, catalase, glutathione peroxidase, a TGFβ inhibitor, VEGF, sonic hedgehog protein, FGF-1, FGF-2, HGF, and IAPs.

The present disclosure provides for a method of treating a subject suffering from a metabolic defect that damages the heart comprising administering, to the subject, a therapeutically effective amount of a complex comprising a CTP of any one of SEQ ID NOs: 1-35, for example SEQ ID NO: 5, linked to a cargo, where the cargo corrects the metabolic defect.

The present disclosure provides for a method of treating a subject suffering from Gaucher's disease comprising administering, to the subject, a therapeutically effective amount of a complex comprising a CTP of any one of SEQ ID NOs: 1-35, for example SEQ ID NO: 5, linked to a glucocerebrosidase.

Where the CTP of any one of SEQ ID NOs: 1-35, for example SEQ ID NO: 5/cargo complex is administered to a subject, the subject may be a human subject or a non-human subject, such as a primate, a companion animal (e.g., dog, cat, horse) a laboratory animal (e.g., mouse, rat, rabbit or guinea pig) or a farm animal (cow, goat, etc.).

The CTP of any one of SEQ ID NOs: 1-35, for example SEQ ID NO: 5-cargo complex may be administered by any route including but not limited to intravenous, intraarterial, intraperitoneal, subcutaneous, oral, rectal, etc.

The present disclosure provides for pharmaceutical compositions comprising CTP of any one of SEQ ID NOs: 1-35, for example, SEQ ID NO: 5-cargo and a suitable pharmaceutical carrier, for example, water, physiologic saline.

In one aspect, the present disclosure provides a method of treating a human subject suffering from atrial and/or ventricular arrhythmias, comprising introducing a cargo into a cardiac muscle cell of the human subject by administering to the human subject a $CTP_{12aa}$ comprising the sequence of APWHLSSQYSRT (SEQ ID NO: 1), a $CTP_{6aa}$ having a sequence of SQYSRT (SEQ ID NO: 5), or a $CTP_{12aa}$ having a sequence of AAWHLSSQYSRT (SEQ ID NO: 2 (CTP-P2A)) conjugated to a moiety having antiarrhythmic properties, for example amiodarone. In certain embodiments, the present disclosure provides a method of treating ventricular arrhythmias selected from premature ventricular contractions, ventricular tachycardia, and ventricular fibrillation, by administering to the human subject a $CTP_{12aa}$ comprising the sequence of APWHLSSQYSRT (SEQ ID NO: 1), a $CTP_{6aa}$ having a sequence of SQYSRT (SEQ ID NO: 5), or a $CTP_{12aa}$ having a sequence of AAWHLSSQYSRT (SEQ ID NO: 2 (CTP-P2A)) conjugated to a moiety having antiarrhythmic properties, for example amiodarone.

In one aspect, the present disclosure provides a method of treating a human subject suffering from SHF, comprising introducing a cargo into a cardiac muscle cell of the human subject by administering to the human subject a $CTP_{12aa}$ comprising the sequence of APWHLSSQYSRT (SEQ ID NO: 1), a $CTP_{6aa}$ having a sequence of SQYSRT (SEQ ID NO: 5), or a $CTP_{12aa}$ having a sequence of AAWHLSSQYSRT (SEQ ID NO: 2 (CTP-P2A)) conjugated to Neuregulin-1β.

In one aspect, the present disclosure provides a method of performing myocardial perfusion analysis of a subject, by administering to the subject a conjugate of the CTP comprising, for example, SEQ ID NO: 1, 2, 4, or 5 (e.g., an antiarrhythmic-CTP or Neuregulin-1β-CTP), and monitoring through Planar or SPECT imaging, delivery of the conjugate to the subject's heart.

In another aspect, the present disclosure provides a method of imaging or detecting a heart tissue, by administering to the subject a conjugate of the CTP comprising, for example, SEQ ID NO: 1 (e.g., an antiarrhythmic-CTP or Neuregulin-1β-CTP); exposing the subject to conditions conducive to detection of the CTP conjugate; and obtaining an image. In this aspect, the antiarrhythmic-CTP optionally further comprises a detectable moiety.

Where a conjugate of the CTP comprising, for example, SEQ ID NO: 1 (e.g., an antiarrhythmic-CTP or Neuregulin-1β-CTP) is administered to a subject, the subject may be a human subject or a non-human subject, such as a primate, a companion animal (e.g., dog, cat, horse) a laboratory animal (e.g., mouse, rat, rabbit or guinea pig) or a farm animal (cow, goat, etc.).

A conjugate of the CTP comprising, for example, SEQ ID NO: 1, 2, 4, or 5 (e.g., an antiarrhythmic-CTP or Neuregulin-1β-CTP) may be administered by any route including but not limited to intravenous, intraatrial, intraperitoneal, subcutaneous, oral, rectal, etc.

The present disclosure provides for pharmaceutical compositions comprising a conjugate of the CTP comprising, for example, SEQ ID NO: 1, 2, 4, or 5 (e.g., an antiarrhythmic-CTP or Neuregulin-1β-CTP) and a suitable pharmaceutical carrier, for example, water or physiologic saline.

VI. Pharmaceutical Compositions

For therapeutic use, a CTP of any one of SEQ ID NOs: 1-35, for example SEQ ID NO: 5, linked to a therapeutic agent (for example, amiodarone) described herein preferably is combined with a pharmaceutically acceptable carrier. The term "pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable carrier" as used herein refers to buffers, carriers, and excipients suitable for use in contact with the tissues of human beings and animals without excessive toxicity, irritation, allergic response, or other problem or complication, commensurate with a reasonable benefit/risk ratio. Pharmaceutically acceptable carriers include any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see, e.g., Martin, Remington's Pharmaceutical Sciences, 15th Ed., Mack Publ. Co., Easton, PA [1975]. Pharmaceutically acceptable carriers include buffers, solvents, dispersion media, coatings, isotonic and absorption delaying agents, and the like, that are compatible with pharmaceutical administration. The use of such media and agents for pharmaceutically active substances is known in the art.

In certain embodiments, the CTP of any one of SEQ ID NOs: 1-35, for example SEQ ID NO: 5, linked to a therapeutic agent (for example, amiodarone) can be formulated, or co-administered (either at the same time or sequentially), for example, by an enteral route (e.g., orally), with a pH increasing agent, for example, a protein pump inhibitor (PPI), to enhance the stability of the CTP of any one of SEQ ID NOs: 1-35, for example SEQ ID NO: 5, for example, in an acidic environment, for example, in the gastrointestinal tract.

Proton pump inhibitors are a group of drugs whose main action is pronounced and long-lasting reduction of gastric acid production. Proton pump inhibitors act by blocking the hydrogen/potassium adenosine triphosphatase enzyme system (the H$^+$/K$^+$ ATPase, or more commonly just gastric proton pump) of the gastric parietal cell. The proton pump is the terminal stage in gastric acid secretion, being directly responsible for secreting H$^+$ ions into the gastric lumen, making it an ideal target for inhibiting acid secretion. Examples of proton pump inhibitors include: Omeprazole (brand names: LOSEC®, PRILOSEC®, ZEGERID®); Lansoprazole (brand names: PREVACID®, ZOTON®, INHIBITOL®); Esomeprazole (brand names: NEXIUM®); and Pantoprazole (brand names: PROTONIX®, SOMAC®, PANTOLOC®).

Pharmaceutical compositions containing a CTP of any one of SEQ ID NOs: 1-35, for example SEQ ID NO: 5, linked to a therapeutic agent (for example, amiodarone) disclosed herein can be presented in a dosage unit form and can be prepared by any suitable method. A pharmaceutical composition should be formulated to be compatible with its intended route of administration. The pharmaceutical compositions may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form will depend upon the intended mode of administration and therapeutic application.

Although the compositions preferably are formulated for administration enterally (for example, orally), such compositions can be administered by a parenteral mode (e.g., intravenous, subcutaneous, intraperitoneal, or intramuscular injection). The phrases "parenteral administration" and "administered parenterally" as used herein mean modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and infrasternal injection and infusion.

The composition can be formulated as a solution, microemulsion, dispersion, liposome, or other ordered structure suitable for stable storage at high concentration. Sterile injectable solutions can be prepared by incorporating an agent described herein in the required amount in an appropriate solvent with one or a combination of ingredients enumerated above, as required, followed by filtered sterilization. Generally, dispersions are prepared by incorporating an agent described herein into a sterile vehicle that contains a basic dispersion medium and the required other ingredients from those enumerated above. In the case of sterile powders for the preparation of sterile injectable solutions, the preferred methods of preparation are vacuum drying and freeze drying that yield a powder of an agent described herein plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

Depending upon the mode of administration, for example, by parenteral administration, it may be desirable to produce a pharmaceutical formulation that is sterile. Sterilization can be accomplished by any suitable method, e.g., filtration through sterile filtration membranes. Where the composition is lyophilized, filter sterilization can be conducted prior to or following lyophilization and reconstitution.

In certain embodiments, a disclosed composition comprises a polyionic reagent which may, e.g., coat the CTP of any one of SEQ ID NOs: 1-35, for example SEQ ID NO: 5, linked to a therapeutic agent (for example, amiodarone), i.e., the composition comprises a polyionic coating. Exemplary polyionic reagents include PSS (poly(Sodium 4-styrene-sulfonate), PAA (poly Acrylic acid sodium salt), PMG (poly(methylene-co-guanidine) hydrochloride), DS (dextran sulfate), PMA (poly(methyl acrylate)), or PVS (polyvinyl-siloxane).

Lyophilized Formulation

The lyophilized formulation for use in a method of treatment of the present disclosure includes the Cardiac-specific Targeting-Peptide (CTP) (e.g., any one of SEQ ID NOs: 1-35) linked to a drug or therapeutic (e.g., amiodarone) and a lyoprotectant. In certain embodiments, the lyophilized formulation for use in a method of treatment of the present disclosure includes the $CTP_{12aa}$ of SEQ ID NO: 1 linked to a drug or therapeutic (e.g., amiodarone) and a lyoprotectant. In certain embodiments, the lyophilized formulation for use in a method of treatment of the present disclosure includes the $CTP_{12aa}$ of SEQ ID NO: 2 linked to a drug or therapeutic (e.g., amiodarone) and a lyoprotectant. In certain embodiments, the lyophilized formulation for use in a method of treatment of the present disclosure includes the $CTP_{6aa}$ of SEQ ID NO: 5 linked to a drug or therapeutic (e.g., amiodarone) and a lyoprotectant. In certain embodiments, the lyoprotectant may be sugar, e.g., disaccharides. In certain embodiments, the lyoprotectant may be sucrose or maltose. In certain embodiments, the lyophilized formulation may also include one or more of a buffering agent, a surfactant, a bulking agent, and/or a preservative.

The amount of sucrose or maltose useful for stabilization of the lyophilized drug product may be in a weight ratio of at least 1:2 protein to sucrose or maltose. In certain embodiments, the protein to sucrose or maltose weight ratio may be of from 1:2 to 1:5.

In certain embodiments, the pH of the formulation, prior to lyophilization, may be set by addition of a pharmaceutically acceptable acid and/or base. In certain embodiments the pharmaceutically acceptable acid may be hydrochloric acid. In certain embodiments, the pharmaceutically acceptable base may be sodium hydroxide.

Before lyophilization, the pH of the solution containing the protein of the present disclosure may be adjusted between about 6 to about 8. In certain embodiments, the pH range for the lyophilized drug product may be from about 7 to about 8.

In certain embodiments, a salt or buffer components may be added in an amount of about 10 mM-about 200 mM. The salts and/or buffers are pharmaceutically acceptable and are derived from various known acids (inorganic and organic) with "base forming" metals or amines. In certain embodiments, the buffer may be phosphate buffer. In certain embodiments, the buffer may be glycinate, carbonate, citrate buffers, in which case, sodium, potassium or ammonium ions can serve as counterion.

In certain embodiments, a "bulking agent" may be added. A "bulking agent" is a compound which adds mass to a lyophilized mixture and contributes to the physical structure of the lyophilized cake (e.g., facilitates the production of an essentially uniform lyophilized cake which maintains an open pore structure). Illustrative bulking agents include mannitol, glycine, polyethylene glycol and sorbitol. The lyophilized formulations of the present disclosure may contain such bulking agents.

A preservative may be optionally added to the formulations herein to reduce bacterial action. The addition of a preservative may, for example, facilitate the production of a multi-use (multiple-dose) formulation.

In certain embodiments, the lyophilized drug product for use in a method of treatment of the present disclosure may be constituted with an aqueous carrier. The aqueous carrier of interest herein is one which is pharmaceutically acceptable (e.g., safe and non-toxic for administration to a human) and is useful for the preparation of a liquid formulation, after lyophilization. Illustrative diluents include sterile water for injection (SWFI), bacteriostatic water for injection (BWFI), a pH buffered solution (e.g. phosphate-buffered saline), sterile saline solution, Ringer's solution or dextrose solution.

In certain embodiments, the lyophilized drug product of the current disclosure is reconstituted with either Sterile Water for Injection, USP (SWFI) or 0.9% Sodium Chloride Injection, USP. During reconstitution, the lyophilized powder dissolves into a solution.

In certain embodiments, the lyophilized protein product of the instant disclosure is constituted to about 4.5 mL water for injection and diluted with 0.9% saline solution (sodium chloride solution).

Liquid Formulation

In embodiments, the Cardiac-specific Targeting-Peptide (CTP) (e.g., any one of SEQ ID NOs: 1-35) linked to a drug or therapeutic (e.g., amiodarone) of the present disclosure is formulated as a liquid formulation for use in a method of treatment described herein. The liquid formulation may be presented at a 10 mg/mL concentration in either a USP/Ph Eur type I 50R vial closed with a rubber stopper and sealed with an aluminum crimp seal closure. The stopper may be made of elastomer complying with USP and Ph Eur. In certain embodiments vials may be filled with an effective amount of the CTP conjugated to a drug or therapeutic solution in order to allow an extractable volume. In certain embodiments, the liquid formulation may be diluted with 0.9% saline solution.

In certain embodiments, the liquid formulation for use in a method of the disclosure may be prepared as a solution in combination with a sugar at stabilizing levels. In certain embodiments the liquid formulation may be prepared in an aqueous carrier. In certain embodiments, a stabilizer may be added in an amount no greater than that which may result in a viscosity undesirable or unsuitable for intravenous administration. In certain embodiments, the sugar may be disaccharides, e.g., sucrose. In certain embodiments, the liquid formulation may also include one or more of a buffering agent, a surfactant, and a preservative.

In certain embodiments, the pH of the liquid formulation may be set by addition of a pharmaceutically acceptable acid and/or base. In certain embodiments, the pharmaceutically acceptable acid may be hydrochloric acid. In certain embodiments, the base may be sodium hydroxide.

In addition to aggregation, deamidation is a common product variant of peptides and proteins that may occur during fermentation, harvest/cell clarification, purification, drug substance/drug product storage and during sample analysis. Deamidation is the loss of $NH_3$ from a protein forming a succinimide intermediate that can undergo hydrolysis. The succinimide intermediate results in a 17 unit mass decrease of the parent peptide. The subsequent hydrolysis results in an 18 unit mass increase. Isolation of the succinimide intermediate is difficult due to instability under aqueous conditions. As such, deamidation is typically detectable as 1 unit mass increase. Deamidation of an asparagine results in either aspartic or isoaspartic acid. The parameters affecting the rate of deamidation include pH, temperature, solvent dielectric constant, ionic strength, primary sequence, local polypeptide conformation and tertiary structure. The amino acid residues adjacent to Asn in the peptide chain affect deamidation rates. Gly and Ser following an Asn in protein sequences results in a higher susceptibility to deamidation.

In certain embodiments, the liquid formulation for use in a method of treatment described in the present disclosure may be preserved under conditions of pH and humidity to prevent deamidation of the protein product.

The aqueous carrier of interest herein is one which is pharmaceutically acceptable (safe and non-toxic for administration to a human) and is useful for the preparation of a liquid formulation. Illustrative carriers include sterile water for injection (SWFI), bacteriostatic water for injection (BWFI), a pH buffered solution (e.g. phosphate-buffered saline), sterile saline solution, Ringer's solution or dextrose solution.

A preservative may be optionally added to the formulations herein to reduce bacterial action. The addition of a preservative may, for example, facilitate the production of a multi-use (multiple-dose) formulation.

Intravenous (IV) formulations may be the preferred administration route in particular instances, such as when a patient is in the hospital after transplantation receiving all drugs via the IV route. In certain embodiments, the liquid formulation is diluted with 0.9% Sodium Chloride solution before administration. In certain embodiments, the diluted drug product for injection is isotonic and suitable for administration by intravenous infusion.

In certain embodiments, a salt or buffer component may be added in an amount of 10 mM-200 mM. The salts and/or buffers are pharmaceutically acceptable and are derived from various known acids (inorganic and organic) with "base forming" metals or amines. In certain embodiments, the buffer may be phosphate buffer. In certain embodiments, the buffer may be glycinate, carbonate, citrate buffers, in which case, sodium, potassium or ammonium ions can serve as counterion.

A preservative may be optionally added to the formulations herein to reduce bacterial action. The addition of a preservative may, for example, facilitate the production of a multi-use (multiple-dose) formulation.

The aqueous carrier of interest herein is one which is pharmaceutically acceptable (safe and non-toxic for administration to a human) and is useful for the preparation of a liquid formulation. Illustrative carriers include sterile water for injection (SWFI), bacteriostatic water for injection (BWFI), a pH buffered solution (e.g. phosphate-buffered saline), sterile saline solution, Ringer's solution or dextrose solution.

A preservative may be optionally added to the formulations herein to reduce bacterial action. The addition of a preservative may, for example, facilitate the production of a multi-use (multiple-dose) formulation.

In another aspect the present disclosure also provides sustained release formulations (long-lasting formulation) suitable for injection to deliver a comprising Cardiac-specific Targeting-Peptide (CTP) conjugated to Neuregulin-1β or a moiety having antiarrhythmic properties.

VII. Dosage Regimen

In one aspect, provided herein is sustained-delivery formulation of a peptide comprising a Cardiac-specific Targeting-Peptide (CTP) (e.g., any one of SEQ ID NOs: 1-35) linked to a drug or therapeutic (e.g., amiodarone). In certain embodiments, the formulation uses a controlled release system. In certain embodiments, the formulation uses a slow release system. In certain embodiments, a sustained-delivery formulation of the present disclosure includes a peptide comprising a $CTP_{12aa}$ (SEQ ID NO: 1) linked to a therapeutic agent (e.g., amiodarone). In certain embodiments, a sustained-delivery formulation of the present disclosure includes a peptide comprising a $CTP_{12aa}$ (SEQ ID NO: 2) linked to a therapeutic agent (e.g., amiodarone). In certain embodiments, a sustained-delivery formulation of the present disclosure includes a peptide comprising a $CTP_{6aa}$ (SEQ ID NO: 5) linked to a therapeutic agent (e.g., amiodarone).

In certain embodiments, the formulation delivers a peptide comprising a Cardiac-specific Targeting-Peptide (CTP) (e.g., any one of SEQ ID NOs: 1-35) of the present disclosure linked to a therapeutic agent (e.g., amiodarone) over a period of at least 6 hours (e.g., 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours). In certain embodiments, the formulation delivers a peptide comprising a $CTP_{12aa}$ represented by SEQ ID NO: 1 linked to a drug or therapeutic (e.g., amiodarone) over a period of at least 6 hours (e.g., 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours). In certain embodiments, the formulation delivers a peptide comprising a $CTP_{12aa}$ represented by SEQ ID NO: 2 linked to a drug or therapeutic (e.g., amiodarone) over a period of at least 6 hours (e.g., 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours). In certain embodiments, the formulation delivers a peptide comprising a $CTP_{6aa}$ represented by SEQ ID NO: 5 linked to a drug or therapeutic (e.g., amiodarone) over a period of at least 6 hours (e.g., 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, or 24 hours).

In certain embodiments, the formulation delivers a peptide of the present disclosure (e.g., any one of SEQ ID NOs: 1-35) linked to a therapeutic agent (e.g., amiodarone) over a period of 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, or 24 hours. In certain embodiments, the formulation delivers a peptide comprising a $CTP_{12aa}$ represented by SEQ ID NO: 1 linked to a drug or therapeutic (e.g., amiodarone) over a period of 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, or 24 hours. In certain embodiments, the formulation delivers a peptide comprising a $CTP_{12aa}$ represented by SEQ ID NO: 2 linked to a drug or therapeutic (e.g., amiodarone) over a period of 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, or 24 hours. In certain embodiments, the formulation delivers a peptide comprising a $CTP_{6aa}$ represented by SEQ ID NO: 5 linked to a drug or therapeutic (e.g., amiodarone) over a period of 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, or 24 hours.

In certain embodiments, the formulation delivers a peptide of the present disclosure (e.g., any one of SEQ ID NOs: 1-35) linked to a therapeutic agent (e.g., amiodarone) at least once daily (e.g., once a day, twice a day, three times a day). In certain embodiments, the formulation delivers a peptide comprising a $CTP_{12aa}$ represented by SEQ ID NO: 1 linked to a drug or therapeutic (e.g., amiodarone) at least once daily (e.g., once a day, twice a day, three times a day). In certain embodiments, the formulation delivers a peptide comprising a $CTP_{12aa}$ represented by SEQ ID NO: 2 linked to a drug or therapeutic (e.g., amiodarone) at least once daily (e.g., once a day, twice a day, three times a day). In certain embodiments, the formulation delivers a peptide comprising a $CTP_{6aa}$ represented by SEQ ID NO: 5 linked to a drug or therapeutic (e.g., amiodarone) at least once daily (e.g., once a day, twice a day, three times a day).

In certain embodiments, the formulation delivering a peptide of the present disclosure (e.g., any one of SEQ ID NOs: 1-35) linked to a therapeutic agent (e.g., amiodarone) is administered at least once a week (e.g., once a week, twice a week, 3, 4, 5, 6, 7, or more times a week). In certain embodiments, the formulation delivering a peptide comprising a $CTP_{12aa}$ represented by SEQ ID NO: 1 linked to a drug or therapeutic (e.g., amiodarone) is administered at least once a week (e.g., once a week, twice a week, 3, 4, 5, 6, 7, or more times a week). In certain embodiments, the formulation delivering a peptide comprising a $CTP_{12aa}$ represented by SEQ ID NO: 2 linked to a drug or therapeutic (e.g., amiodarone) is administered at least once a week (e.g., once a week, twice a week, 3, 4, 5, 6, 7, or more times a week). In certain embodiments, the formulation delivering a peptide comprising a $CTP_{6aa}$ represented by SEQ ID NO: 5 linked to a drug or therapeutic (e.g., amiodarone) is administered at least once a week (e.g., once a week, twice a week, 3, 4, 5, 6, 7, or more times a week).

In some embodiments, the formulation delivering a peptide of the present disclosure (e.g., any one of SEQ ID NOs: 1-35) linked to a therapeutic agent (e.g., amiodarone) is a sustained release formulation administered about once per month, about once per every 2 months, about once per every 3 months, about once per every 2 weeks, about once per every 3 weeks, about once per every 4 weeks, about once per every 5 weeks, about once per every 6 weeks, about once per every 7 weeks, about once per every 8 weeks, about once per every 9 weeks, or about once per every 10 weeks. In certain embodiments, the formulation delivering a peptide comprising a $CTP_{12aa}$ represented by SEQ ID NO: 1 linked to a drug or therapeutic (e.g., amiodarone) is a sustained release formulation administered about once per month, about once per every 2 months, about once per every 3 months, about once per every 2 weeks, about once per every 3 weeks, about once per every 4 weeks, about once per every 5 weeks, about once per every 6 weeks, about once per every 7 weeks, about once per every 8 weeks, about once per every 9 weeks, or about once per every 10 weeks. In certain embodiments, the formulation delivering a peptide comprising a $CTP_{12aa}$ represented by SEQ ID NO: 2 linked to a drug or therapeutic (e.g., amiodarone) is a sustained release formulation administered about once per month, about once per every 2 months, about once per every 3 months, about once per every 2 weeks, about once per every 3 weeks, about once per every 4 weeks, about once per every 5 weeks, about once per every 6 weeks, about once per every 7 weeks, about once per every 8 weeks, about once per every 9 weeks, or about once per every 10 weeks. In certain embodiments, the formulation delivering a peptide comprising a $CTP_{6aa}$ represented by SEQ ID NO: 5 linked to a drug or therapeutic (e.g., amiodarone) is a sustained release formulation administered about once per month, about once per every 2 months, about once per every 3 months, about once per every 2 weeks, about once per every 3 weeks, about once per every 4 weeks, about once per every 5 weeks, about once per every 6 weeks, about once per every 7 weeks, about once per every 8 weeks, about once per every 9 weeks, or about once per every 10 weeks.

In some embodiments, a peptide of the present disclosure (e.g., any one of SEQ ID NOs: 1-35) linked to a therapeutic agent (e.g., amiodarone or Neuregulin-1β) is administered at a rate of about 100 mg, 200 mg, 300 mg, 400 mg, 500 mg, 600 mg, 700 mg, 800 mg, 900 mg, 1000 mg, 1100 mg, 1200 mg, 1300 mg, 1400 mg, 1500 mg, 1600 mg, 1700 mg, 1800 mg, 1900 mg, or 2000 mg over a period of 24 hours, for example, the first 24 hour period of administration. In some embodiments, a formulation described herein is administered at a rate of between 100 mg and 500 mg, between 100 mg and 1000 mg, between 500 mg and 1000 mg, between 700 mg and 1000 mg, between 700 mg and 1500 mg, between 1200 mg and 1500 mg, between 1000 mg and 1500 mg, between 1000 mg and 2000 mg, between 1500 mg and 2000 mg, between 1700 mg and 2000 mg, between 800 mg and 1200 mg, between 800 mg and 1000 mg, between 800 mg and 1600 mg, between 600 mg and 800 mg, between 400 mg and 600 mg, or between 900 and 1200 mg over a period of 24 hours, for example, the first 24 hour period of administration. In some embodiments, a peptide of the present disclosure (e.g., any one of SEQ ID NOs: 1-35) linked to a therapeutic agent (e.g., amiodarone or Neuregulin-1β) is administered in the form of a formulation that is administered orally, intravenously, enterally, parenterally, topically, by injection, intramuscularly, intraarterially, intrathecally, intracapsularly, intraorbitally, intracardiacly, intradermally, intraperitoneally, transtracheally, subcutaneously, subcuticularly, intraarticularly, subcapsularly, subarachnoidally, intraspinally, by epidural or infrasternal injection, or by infusion.

In some embodiments, a formulation described herein can be administered by an infusion protocol. For example, in some embodiments, a formulation can be administered, for example, by infusion, for example, in the form of a saline solution, where the solution includes a peptide of the present disclosure (e.g., any one of SEQ ID NOs: 1-35) linked to a therapeutic agent (e.g., amiodarone or Neuregulin-1β). In some embodiments the peptide linked to a therapeutic agent is administered to a patient in an amount of about 25 mg, 50 mg, 75 mg, 100 mg, 110 mg, 125 mg, 130 mg, 140 mg, 150 mg, 160 mg, 175 mg, 200 mg, 225 mg, 250 mg, 275 mg, 300 mg, 325 mg, 350 mg, 360 mg, 375 mg, 400 mg, 450 mg, 500 mg, 600 mg, 700 mg, 720 mg, 750 mg, 0 mg to 100 mg, 50 mg to 150 mg, 50 mg, to 100 mg, 100 mg to 200 mg, 200 mg to 300 mg, 200 mg to 400 mg, 200 mg to 500 mg, 100 mg to 150 mg, 100 mg to 500 mg, 150 mg to 300 mg, 100 mg to 360 mg, 100 mg to 400 mg, 300 mg to 500 mg, 300 mg to 600 mg, 300 mg to 600 mg, or 300 mg to 700 mg over a period of about 5 minutes, 10 minutes, 20 minutes, 30 minutes, 40 minutes, 50 minutes, 60 minutes, 90 minutes, 2 hours, 3 hours, 4 hours, 5 hours, 6 hours, 7 hours, 8 hours 9 hours 10 hours, 11 hours, 12 hours, 13 hours, 14 hours 15 hours 16 hours 17 hours, 18 hours, 1 day, 2 days, 3 days 4 days, 5 days, 6 days, or 1 week.

In some embodiments, a formulation described herein can be administered by an infusion protocol. For example, in some embodiments, a formulation can be administered, for example, by infusion, for example, in the form of a saline solution, where the solution includes a peptide of the present disclosure (e.g., any one of SEQ ID NOs: 1-35) linked to a therapeutic agent (e.g., amiodarone or Neuregulin-1β). In some embodiments the peptide linked to a therapeutic agent is administered to a patient in an amount of about 25 mg, 50 mg, 75 mg, 100 mg, 110 mg, 125 mg, 130 mg, 140 mg, 150 mg, 160 mg, 175 mg, 200 mg, 225 mg, 250 mg, 275 mg, 300 mg, 350 mg, 400 mg, 450 mg, 500 mg, 0 mg to 100 mg, 50 mg to 150 mg, 50 mg, to 100 mg, 100 mg to 200 mg, 200 mg to 300 mg, 200 mg to 400 mg, 200 mg to 500 mg, 100 mg to 150 mg, 100 mg to 500 mg, or 150 mg to 300 mg over about the first 1 minute, 3 minutes, 5 minutes, 7 minutes, 10 minutes, 12 minutes, 15 minutes, 20 minutes, or 30 minutes of infusion; after which the peptide linked to the therapeutic agent is administered to the patient in an amount of about 25 mg, 50 mg, 75 mg, 100 mg, 110 mg, 125 mg, 130 mg, 140 mg, 150 mg, 160 mg, 175 mg, 200 mg, 225 mg, 250 mg, 275 mg, 300 mg, 325 mg, 350 mg, 360 mg, 375 mg, 400 mg, 450 mg, 500 mg, 600 mg, 700 mg, 720 mg, 750 mg, 0 mg to 100 mg, 50 mg to 150 mg, 50 mg, to 100 mg, 100 mg to 200 mg, 200 mg to 300 mg, 200 mg to 400 mg, 200 mg to 500 mg, 100 mg to 150 mg, 100 mg to 500 mg, 150 mg to 300 mg, 100 mg to 360 mg, 100 mg to 400 mg, 300 mg to 500 mg, 300 mg to 600 mg, 300 mg to 600 mg, or 300 mg to 700 mg over the next 1 hour, 2 hours, 3 hours, 4 hours, 5 hours, 6 hours, 7 hours, 8 hours, 9 hours, 10 hours, 11 hours, 12 hours, 13 hours, 14 hours, or 15 hours of infusion; after which the peptide linked to the therapeutic agent is administered to the patient in an amount of about 25 mg, 50 mg, 75 mg, 100 mg, 110 mg, 125 mg, 130 mg, 140 mg, 150 mg, 160 mg, 175 mg, 200 mg, 225 mg, 250 mg, 275 mg, 300 mg, 325 mg, 350 mg, 360 mg, 375 mg, 400 mg, 450 mg, 475 mg, 500 mg, 510 mg, 520 mg, 530 mg, 540 mg, 550 mg, 560 mg, 570 mg, 580 mg, 590 mg, 600 mg, 700 mg, 720 mg, 750 mg, 800 mg, 900 mg, 950 mg, 1000 mg, 1050 mg, 1080 mg, 0 mg to 100 mg, 50 mg to 150 mg, 50 mg, to 100 mg, 100 mg to 200 mg, 200 mg to 300 mg, 200 mg to 400 mg, 200 mg to 500 mg, 100 mg to 150 mg, 100 mg to 500 mg, 150 mg to 300 mg, 100 mg to 360 mg, 100 mg to 400 mg, 300 mg to 500 mg, 300 mg to 600 mg, 300 mg to 600 mg, or 300 mg to 700 mg, 100 mg to 550 mg, 200 mg to 550 mg, 300 mg to 550 mg, 400 mg to 550 mg, 500 mg to 600 mg, 500 mg to 700 mg, 500 mg to 800 mg, 500 mg to 900 mg, 500 mg to 1000 mg, 500 mg to 1100 mg, or 400 mg to 1100 mg over the next 30 minutes, 1 hour, 2 hours 3 hours, 4 hours, 5 hours, 6 hours, 7 hours, 8 hours, 9 hours, 10 hours, 11 hours, 12 hours, 13 hours, 14 hours, 15 hours, 16 hours, 17 hours 18 hours, 19 hours, 20 hours, 21 hours, 22 hours, 23 hours, 24 hours, 30 hours, or 36 hours of infusion. In a particular embodiment, the peptide linked to the therapeutic agent is administered to the patient in an amount of about 150 mg over the first 10 minutes of infusion, followed by 360 mg over the next 6 hours, and followed by 540 mg over the next 18 hours.

In some embodiments, a formulation described herein is administered, for example, by infusion, where a peptide described herein (e.g., any one of SEQ ID NOs: 1-35) linked to a therapeutic agent (e.g., amiodarone or Neuregulin-1β) is administered at a specified rate after about the first 24 hours of administration. For example, in some embodiments described herein, after the first 24 hours of administration, the peptide linked to a therapeutic agent is administered to a patient in an amount of about 25 mg, 50 mg, 75 mg, 100 mg, 110 mg, 125 mg, 130 mg, 140 mg, 150 mg, 160 mg, 175 mg, 200 mg, 225 mg, 250 mg, 275 mg, 300 mg, 325 mg, 350 mg, 360 mg, 375 mg, 400 mg, 450 mg, 475 mg, 500 mg, 510 mg, 520 mg, 530 mg, 540 mg, 550 mg, 560 mg, 570 mg, 580 mg, 590 mg, 600 mg, 700 mg, 720 mg, 750 mg, 800 mg, 900 mg, 950 mg, 1000 mg, 1050 mg, 1080 mg, 1100 mg, 1200 mg, 1300 mg, 1400 mg, 1500 mg, 1600 mg, 0 mg to 100 mg, 50 mg to 150 mg, 50 mg, to 100 mg, 100 mg to 200 mg, 200 mg to 300 mg, 200 mg to 400 mg, 200 mg to 500 mg, 100 mg to 150 mg, 100 mg to 500 mg, 100 mg to 600 mg, 150 mg to 300 mg, 100 mg to 360 mg, 100 mg to 400 mg, 300 mg to 500 mg, 300 mg to 600 mg, 300 mg to 600 mg, or 300 mg to 700 mg, 100 mg to 550 mg, 200 mg to 550 mg, 300 mg to 550 mg, 400 mg to 550 mg, 400 mg to 600 mg, 500 mg to 600 mg, 500 mg to 700 mg, 500 mg to 800 mg, 500 mg to 900 mg, 500 mg to 1000 mg, 500 mg to 1100 mg, 600 mg to 800 mg, 600 mg to 1000 mg, 1000 mg to 1500 mg, 1000 mg to 1200 mg, 1000 mg to 1400 mg, 1100 mg to 1500 mg, or 400 mg to 1100 mg over 30 minutes, 1 hour, 2 hours 3 hours, 4 hours, 5 hours, 6 hours, 7 hours, 8 hours, 9 hours, 10 hours, 11 hours, 12 hours, 13 hours, 14 hours, 15 hours, 16 hours, 17 hours 18 hours, 19 hours, 20 hours, 21 hours, 22 hours, 23 hours, 24 hours, 27 hours, 30 hours, or 36 hours following the first 24 hours of administration. in a particular embodiment described herein, after the first 24 hours of administration, the peptide linked to a therapeutic agent is administered to a patient in an amount of about 720 mg over 24 hours following the first 24 hours of administration. In embodiments described herein, the aforementioned administration may be continued for a period of about 1 day, 2 days, 3 days, 4 days, 5 days, 6 days, 1 week, 10 days, 12 days, 2 weeks, 15 days, 18 days, 20 days, 3 weeks, 4 weeks, 5 weeks, 6 weeks, 7 weeks, 8 weeks 9 weeks, 10 weeks, 11 weeks, 12 weeks, or longer.

In some embodiments, a formulation described herein is administered, for example, by infusion or subcutaneously, where a peptide described herein (e.g., any one of SEQ ID NOs: 1-35) linked to a therapeutic agent (e.g., amiodarone) is administered to achieve a serum circulating level of the therapeutic of about 10-2500 ng/mL in a patient. For example, in some embodiments described herein, after the first 24 hours of administration, the peptide linked to amiodarone is administered to a patient in an amount to achieve a serum circulating level of about 10 ng/mL, 25 ng/mL, 50 ng/mL, 75 ng/mL, 100 ng/mL, 110 ng/mL, 125 ng/mL, 130 ng/mL, 140 ng/mL, 150 ng/mL, 160 ng/mL, 175 ng/mL, 200 ng/mL, 225 ng/mL, 250 ng/mL, 275 ng/mL, 300 ng/mL, 325 ng/mL, 350 ng/mL, 360 ng/mL, 375 ng/mL, 400 ng/mL, 450 ng/mL, 475 ng/mL, 500 ng/mL, 510 ng/mL, 520 ng/mL, 530 ng/mL, 540 ng/mL, 550 ng/mL, 560 ng/mL, 570 ng/mL, 580 ng/mL, 590 ng/mL, 600 ng/mL, 700 ng/mL, 720 ng/mL, 750 ng/mL, 800 ng/mL, 900 ng/mL, 950 ng/mL, 1000 ng/mL, 1050 ng/mL, 1080 ng/mL, 1100 ng/mL, 1200 ng/mL, 1300 ng/mL, 1400 ng/mL, 1500 ng/mL, 1600 ng/mL, 10 ng/mL to 100 ng/mL, 50 ng/mL to 150 ng/mL, 50 ng/mL to 100 ng/mL, 100 ng/mL to 200 ng/mL, 200 ng/mL to 300 ng/mL, 200 ng/mL to 400 ng/mL, 200 ng/mL to 500 ng/mL, 100 ng/mL to 150 ng/mL, 100 ng/mL to 500 ng/mL, 100 ng/mL to 600 ng/mL, 150 ng/mL to 300 ng/mL, 100 ng/mL to 360 ng/mL, 100 ng/mL to 400 ng/mL, 300 ng/mL to 500 ng/mL, 300 ng/mL to 600 ng/mL, 300 ng/mL to 600 ng/mL, or 300 ng/mL to 700 ng/mL, 100 ng/mL to 550 ng/mL, 200 ng/mL to 550 ng/mL, 300 ng/mL to 550 ng/mL, 400 ng/mL to 550 ng/mL, 400 ng/mL to 600 ng/mL, 500 ng/mL to 600 ng/mL, 500 ng/mL to 700 ng/mL, 500 ng/mL to 800 ng/mL, 500 ng/mL to 900 ng/mL, 500 ng/mL to 1000 ng/mL, 500 ng/mL to 1100 ng/mL, 600 ng/mL to 800 ng/mL, 600 ng/mL to 1000 ng/mL, 1000 ng/mL to 1500 ng/mL, 1000 ng/mL to 1200 ng/mL, 1000 ng/mL to 1400 ng/mL, 1100 ng/mL to 1500 ng/mL, or 400 ng/mL to 1100 ng/mL over 30 minutes, 1 hour, 2 hours 3 hours, 4 hours, 5 hours, 6 hours, 7 hours, 8 hours, 9 hours, 10 hours, 11 hours, 12 hours, 13 hours, 14 hours, 15 hours, 16 hours, 17 hours 18 hours, 19 hours, 20 hours, 21 hours, 22 hours, 23 hours, 24 hours, 27 hours, 30 hours, or 36 hours following the first 24 hours of administration. In a particular embodiment described herein, the peptide of SEQ ID NO: 1, 2, or 5 linked to amiodarone is administered to a patient in an amount to achieve a serum circulating level of amiodarone of about 10 to 2500 ng/mL for 24 hours to 7 days following the first 24 hours of administration. In embodiments described herein, the aforementioned administration may be continued for a period of about 1 day, 2 days, 3 days, 4 days, 5 days, 6 days, 1 week, 10 days, 12 days, 2 weeks, 15 days, 18 days, 20 days, 3 weeks, 4 weeks, 5 weeks, 6 weeks, 7 weeks, 8 weeks 9 weeks, 10 weeks, 11 weeks, 12 weeks, or longer.

VIII. Definitions

The term "CTP" as used herein refers to a Cardiac-specific Targeting-Peptide. In certain embodiments, the CTP is comprised of a 6-amino acid long peptide, $CTP_{6aa}$. In certain embodiments, the $CTP_{12aa}$ a is comprised of a 12-amino acid long peptide. In certain embodiments, the CTP is conjugated to a moiety having antiarrhythmic properties.

The term "effective amount" as used herein refers to the amount of an active agent (e.g., a CTP of any one of SEQ ID NOs: 1-35, for example SEQ ID NO: 1, 2, or 5, of the present disclosure) sufficient to effect beneficial or desired results. An effective amount can be administered in one or more administrations, applications or dosages and is not intended to be limited to a particular formulation or administration route.

As used herein, "treat", "treating," and "treatment" mean the treatment of a disease in a subject, e.g., in a human. This includes: (a) inhibiting the disease, i.e., arresting its development; and (b) relieving the disease, i.e., causing regression of the disease state. As used herein, the terms "subject" and "patient" refer to an organism to be treated by the methods and compositions described herein. Such organisms preferably include, but are not limited to, mammals (e.g., murines, simians, equines, bovines, porcines, canines, felines, and the like), and more preferably includes humans.

The methods and compositions described herein can be used alone or in combination with other therapeutic agents and/or modalities. The term administered "in combination," as used herein, is understood to mean that two (or more) different treatments are delivered to the subject during the course of the subject's affliction with the disorder, such that the effects of the treatments on the patient overlap at a point in time. In certain embodiments, the delivery of one treatment is still occurring when the delivery of the second begins, so that there is overlap in terms of administration. This is sometimes referred to herein as "simultaneous" or "concurrent delivery." In other embodiments, the delivery of one treatment ends before the delivery of the other treatment begins. In certain embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In certain embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

Throughout the description, where compositions are described as having, including, or comprising specific components, or where processes and methods are described as having, including, or comprising specific steps, it is contemplated that, additionally, there are compositions of the present disclosure that consist essentially of, or consist of, the recited components, and that there are processes and methods according to the present disclosure that consist essentially of, or consist of, the recited processing steps.

In the application, where an element or component is said to be included in and/or selected from a list of recited elements or components, it should be understood that the element or component can be any one of the recited elements or components, or the element or component can be selected from a group consisting of two or more of the recited elements or components.

Further, it should be understood that elements and/or features of a composition or a method described herein can be combined in a variety of ways without departing from the spirit and scope of the present disclosure, whether explicit or implicit herein. For example, where reference is made to a particular compound, that compound can be used in various embodiments of compositions of the present disclosure and/or in methods of the present disclosure, unless otherwise understood from the context. In other words, within this application, embodiments have been described and depicted in a way that enables a clear and concise application to be written and drawn, but it is intended and will be appreciated that embodiments may be variously combined or separated without parting from the present teachings and invention(s). For example, it will be appreciated that all features described and depicted herein can be applicable to all aspects of the invention(s) described and depicted herein.

It should be understood that the expression "at least one of" includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

Where the use of the term "about" is before a quantitative value, the present disclosure also includes the specific quantitative value itself, unless specifically stated otherwise. As used herein, the term "about" refers to a 10% variation from the nominal value unless otherwise indicated or inferred.

It should be understood that the order of steps or order for performing certain actions is immaterial so long as the present disclosure remain operable. Moreover, two or more steps or actions may be conducted simultaneously.

The use of any and all examples, or exemplary language herein, for example, "such as" or "including," is intended merely to illustrate better the present disclosure and does not pose a limitation on the scope of the invention unless claimed. No language in the specification should be construed as indicating any non-claimed element as essential to the practice of the present disclosure.

EXAMPLES

The following Examples are merely illustrative and are not intended to limit the scope or content of the invention in any way.

Example 1—Alanine Scan Analysis of the Cardiac-Specific Targeting Peptide

This example describes the design and testing of cardiac-specific targeting peptide variants to determine the contribution of each amino acid residue to transduction activity.

Previous studies had identified a synthetic 12-amino acid peptide (APWHLSSQYSRT; SEQ ID NO: 1) capable of transducing cardiomyocytes. Alanine scanning analysis of the APWHLSSQYSRT (SEQ ID NO: 1) sequence was performed to assess the importance and relative contribution of each amino acid residue to the cell penetrating ability.

Variants of SEQ ID NO: 1 in which every amino acid was systematically mutated to alanine were synthesized in the University of Pittsburgh Peptide Synthesis Facility. Each variant was conjugated to the Cyanine5.5 fluorescent dye (Cy5.5). The rat cardiomyocyte cell line H9C2 (ATCC, catalogue #: CRL-1446) was incubated for 30 minutes at 37° C. with Dimethyl sulfoxide (DMSO) as a control, or the alanine peptide variants. Cells were then washed 3 times with PBS, trypsinized and resuspended, stained for live/dead cells, and then FACS sorted for Cy5.5 positive cells.

Figure 1B:
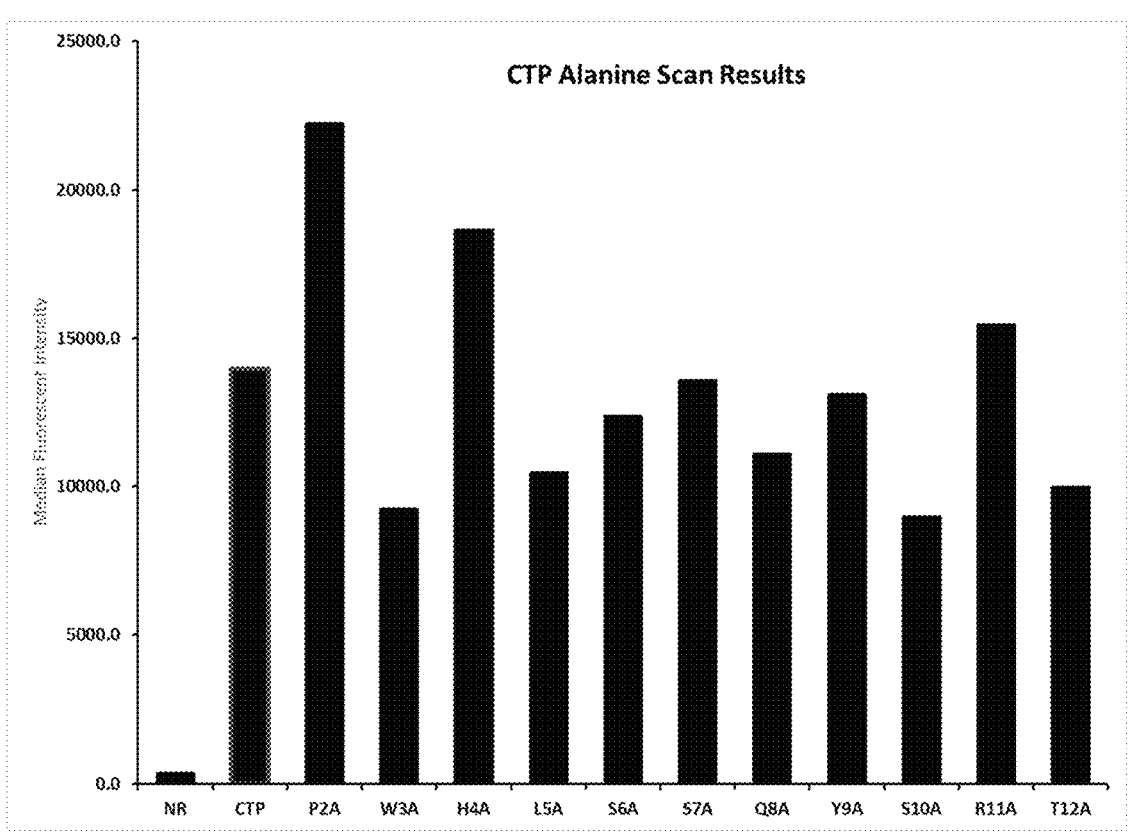

The fluorescence intensities of H9C2 cells transduced with the tested alanine variants are shown in FIG. 1A and FIG. 1B. The percentage of Cy5.5 positive H9C2 cells, normalized to the non-mutated peptide (SEQ ID NO: 1), for each peptide variant is summarized in Table 2 below.

TABLE 2

| SEQ ID NO | Peptide Name | Peptide Sequence | % transduction of H9C2 Cells |
|---|---|---|---|
|  | DMSO | Negative Control | 1.87 |
| 1 | CTP | APWHLSSQYSRT | 100 |
| 2 | P2A | AAWHLSSQYSRT | 59.15 |
| 35 | W3A | APAHLSSQYSRT | 75.81 |
| 26 | H4A | APWALSSQYSRT | 55.05 |
| 27 | L5A | APWHASSQYSRT | 87.81 |
| 28 | S6A | APWHLASQYSRT | 107.21 |
| 29 | S7A | APWHLSAQYSRT | 54.32 |
| 30 | Q8A | APWHLSSAYSRT | 67.35 |
| 31 | Y9A | APWHLSSQASRT | 107 |
| 32 | S10A | APWHLSSQYART | 30.61 |
| 33 | R11A | APWHLSSQYSAT | 32.75 |
| 34 | T12A | APWHLSSQYSRA | 90.33 |

TABLE 3

Figure 1C:
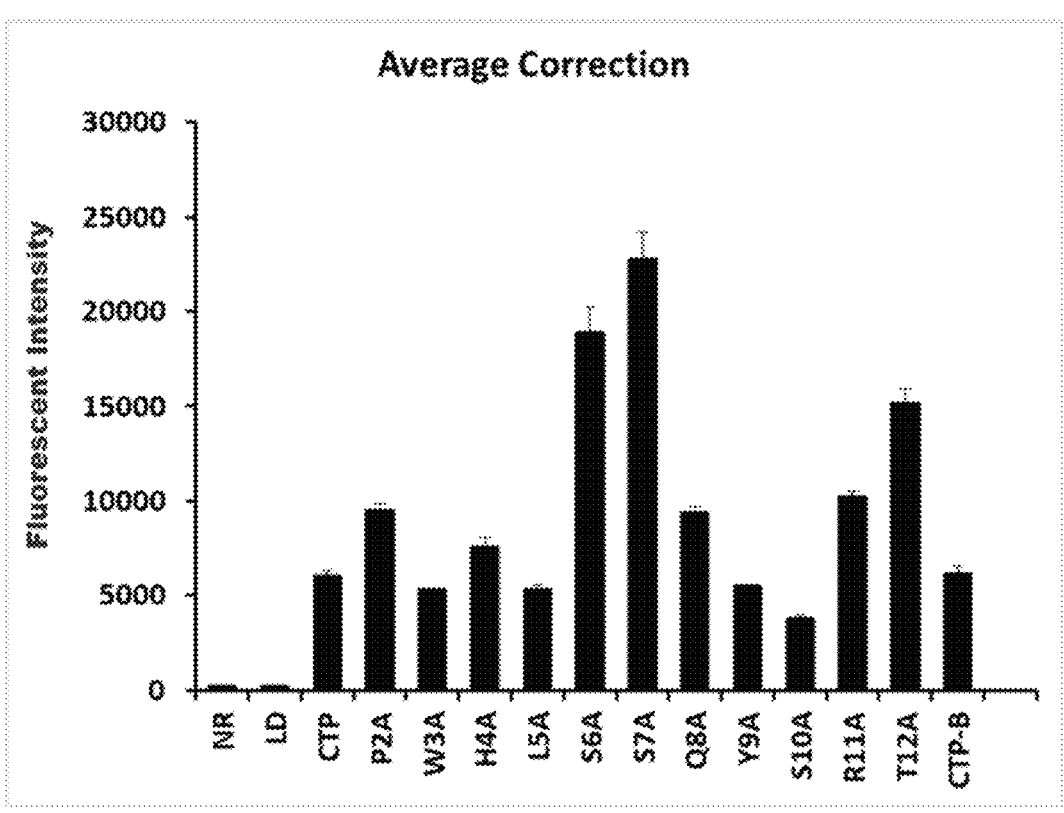

(data represented in FIG. 1C). Fluorescence of the various peptides measured using spectrophotometric data in order to normalize the fluorescence activated cell sorting of H9C2 cells to control for differences in fluorescence between peptides.

| Sample | Average Correction | SD Correction |
|---|---|---|
| No Treatment | 201.7 | 2.5 |
| Live-Dead Stain | 217 | 1.7 |
| CTP | 5996 | 329.2 |
| P2A | 9535.0 | 331.3 |
| W3A | 5332.5 | 64.4 |
| H4A | 7537.1 | 550.1 |
| L5A | 5323.2 | 225.9 |
| S6A | 18868.9 | 1376.7 |
| S7A | 22813.0 | 1396.8 |
| Q8A | 9371.3 | 339.2 |
| Y9A | 5465.9 | 111.5 |
| S10A | 3775.1 | 161.6 |
| R11A | 10255.7 | 254.4 |
| T12A | 15162.7 | 746.5 |
| CTP-B | 6124.6 | 415.1 |

TABLE 4

Figure 1D:
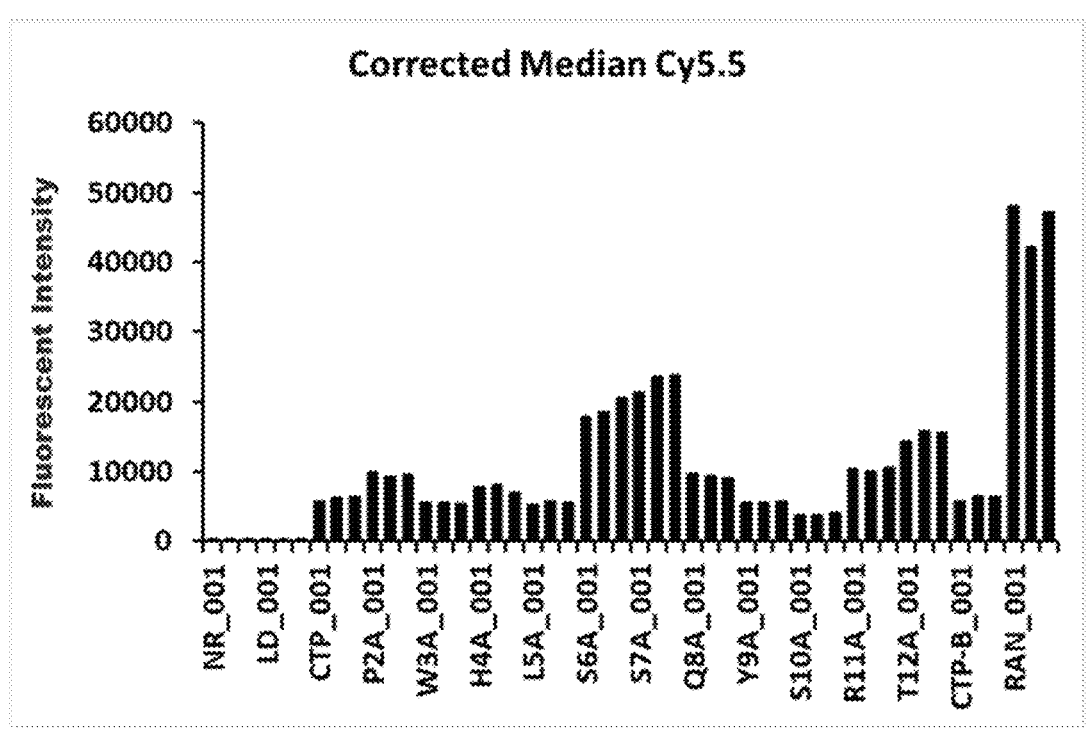

(data represented in FIG. 1D): Fluorescence activated cell sorting of H9C2 cells after a 30 min incubation with 10 uM of various peptides.

| Sample | Raw Median Cy5.5 | Correction Ratio | Corrected Median Cy5.5 |
|---|---|---|---|
| No Treatment_001 | 202 | N/a | 202 |
| No Treatment_002 | 199 | N/a | 199 |
| No Treatment_003 | 204 | N/a | 204 |
| Live-Dead_001 | 216 | N/a | 216 |
| Live-Dead_002 | 216 | N/a | 216 |
| Live-Dead_003 | 219 | N/a | 219 |
| CTP_001 | 5652 | 1 | 5652.0 |
| CTP_002 | 6028 | 1 | 6028.0 |
| CTP_003 | 6308 | 1 | 6308.0 |
| P2A_001 | 9449 | 0.95 | 9901.8 |
| P2A_002 | 8834 | 0.95 | 9298.9 |
| P2A_003 | 9014 | 0.95 | 9488.4 |
| W3A_001 | 4862 | 0.91 | 5369.7 |
| W3A_002 | 4862 | 0.91 | 5369.7 |
| W3A_003 | 4761 | 0.91 | 5258.1 |
| H4A_001 | 7173 | 0.94 | 7666.1 |
| H4A_002 | 7496 | 0.94 | 8011.3 |
| H4A_003 | 6488 | 0.94 | 6934.0 |
| L5A_001 | 3107 | 0.61 | 5077.5 |
| L5A_002 | 3379 | 0.61 | 5522.0 |
| L5A_003 | 3286 | 0.61 | 5370.0 |
| S6A_001 | 22342 | 1.26 | 17793.0 |
| S6A_002 | 23096 | 1.26 | 18393.5 |
| S6A_003 | 25641 | 1.26 | 20420.3 |
| S7A_001 | 20184 | 0.95 | 21208.1 |
| S7A_002 | 22342 | 0.95 | 23475.6 |
| S7A_003 | 22608 | 0.95 | 23755.1 |
| Q8A_001 | 10041 | 1.03 | 9725.5 |
| Q8A_002 | 9642 | 1.03 | 9339.0 |
| Q8A_003 | 9343 | 1.03 | 9049.4 |
| Y9A_001 | 5018 | 0.94 | 5365.7 |
| Y9A_002 | 5093 | 0.94 | 5445.9 |
| Y9A_003 | 5224 | 0.94 | 5586.0 |
| S10A_001 | 1722 | 0.46 | 3707.6 |
| S10A_002 | 1699 | 0.46 | 3658.1 |
| S10A_003 | 1839 | 0.46 | 3959.6 |
| R11A_001 | 9555 | 0.93 | 10237.9 |
| R11A_002 | 9343 | 0.93 | 10010.7 |
| R11A_003 | 9817 | 0.93 | 10518.6 |
| T12A_001 | 18458 | 1.29 | 14307.2 |
| T12A_002 | 20232 | 1.29 | 15682.3 |
| T12A_003 | 19995 | 1.29 | 15498.6 |

TABLE 4-continued (data represented in FIG. 1D): Fluorescence activated cell sorting of
H9C2 cells after a 30 min incubation with 10 uM of various peptides.

| Sample | Raw Median Cy5.5 | Correction Ratio | Corrected Median Cy5.5 |
|---|---|---|---|
| CTP-B_001 | 4711 | 0.831786727 | 5663.7 |
| CTP-B_002 | 5381 | 0.831786727 | 6469.2 |
| CTP-B_003 | 5191 | 0.831786727 | 6240.8 |

These results demonstrated that amino acid residues in the C-terminus of SEQ ID NO: 1 make a major contribution to the transduction ability of the peptide.

Example 2—In Vitro Transduction and Viability Studies of N- and C-Terminal Cardiac-Specific Targeting Peptides The results described in Example 1 suggested that the cell penetrating ability of the cardiac-specific targeting peptide (APWHLSSQYSRT; SEQ ID NO: 1) resides in the 6 C-terminal amino acid residues. To evaluate this further, variants of SEQ ID NO: 1, including linear and cyclized 6-amino acid N- and C-terminal variants, were synthesized in the University of Pittsburgh Peptide Synthesis Facility. Each variant was conjugated to Cy5.5.

Solid-phase peptide synthesis were used to synthesize the full-length form ($NH_2$-APWHLSSQYSRT-COOH (SEQ ID NO: 1)), as well as an N-terminus 6 amino acid called CTP-A ($NH_2$-APWHLS-COOH (SEQ ID NO: 24)), or as $CTP_{6aa}$ ($NH_2$-SQYSRT-COOH (SEQ ID NO: 5)) peptides. Full length and $CTP_{6aa}$ were also synthesized in a cyclic forms. A random, linear, 12-amino acid long peptide (RAN: $NH_2$-STLMKFCYVEQN-COOH (SEQ ID NO: 26)) was also synthesized to serve as control. All peptides were fluorescently labeled with Cyanine5.5 (Cy5.5). Isolated, beating neonatal mouse cardiomyocytes (CMC) were incubated with 10 μM of the peptides at 37° C. for 30 minutes, washed extensively with PBS and confocal microscopy performed. Additionally, H9C2 cells, a rat cardiomyoblast cell line, were incubated with Dimethyl sulfoxide (DMSO) or the peptides labeled with Cy5.5 at 5 μM for 30 minutes at 37° C., washed 3× with PBS, trypsinized and resuspended, stained for live/dead cells, and then FACS sorted for Cy5.5 positive cells.

Figure 2A:
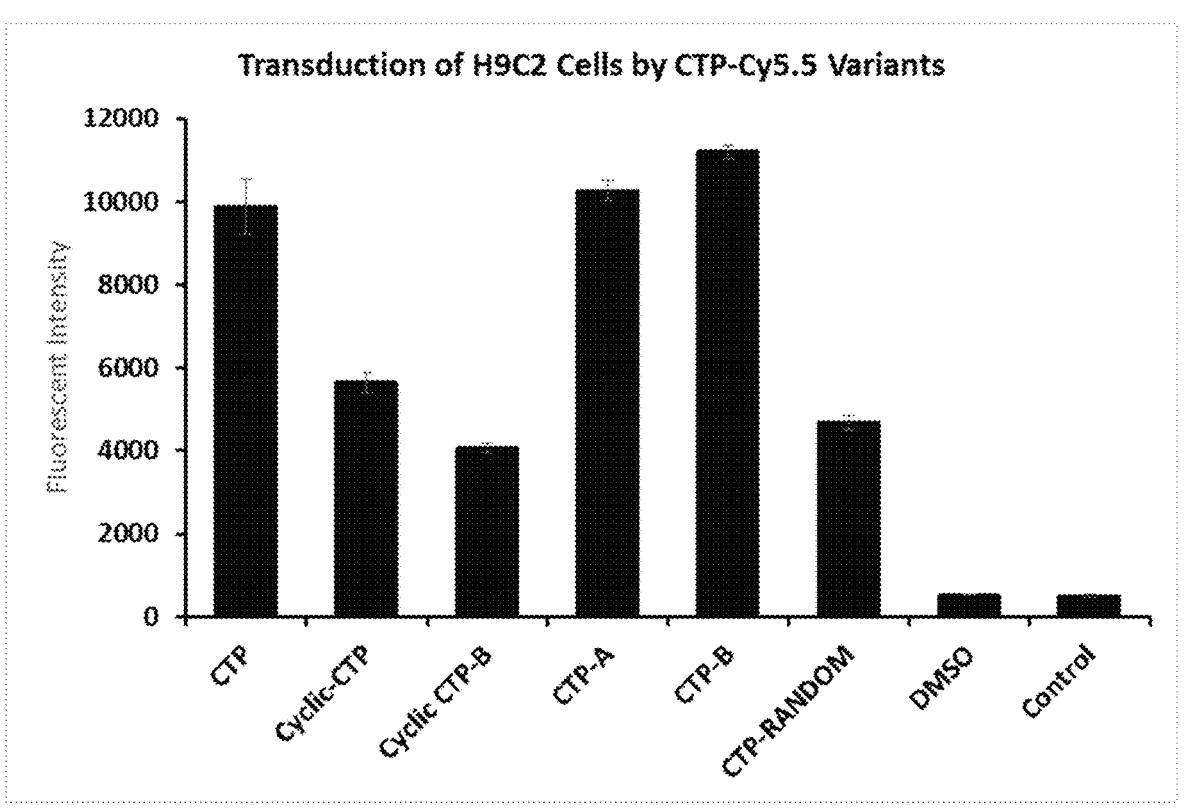
FIGS. 2A-2E are a series of bar graphs that show the transduction efficiencies and viability of various cell types incubated with Cy5.5 labeled cardiac-specific targeting peptide variants.
Figure 2B:
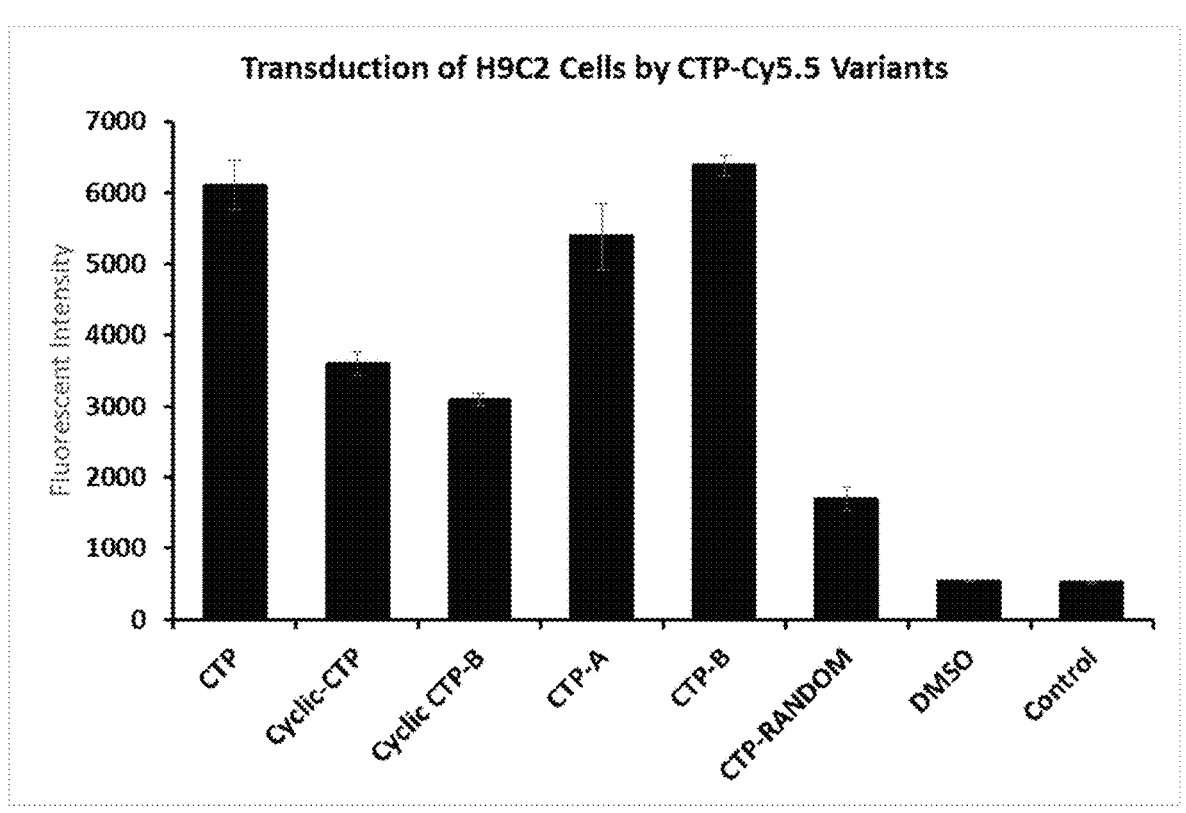
Figure 2C:
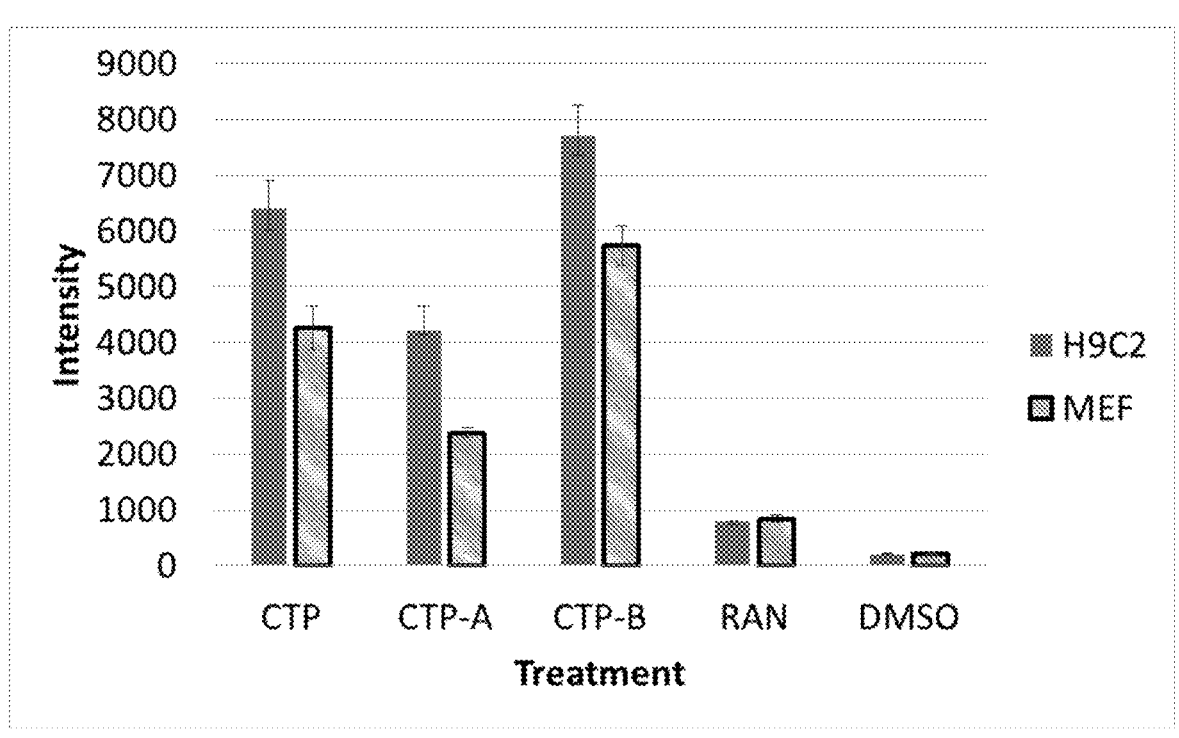
Figure 2D:
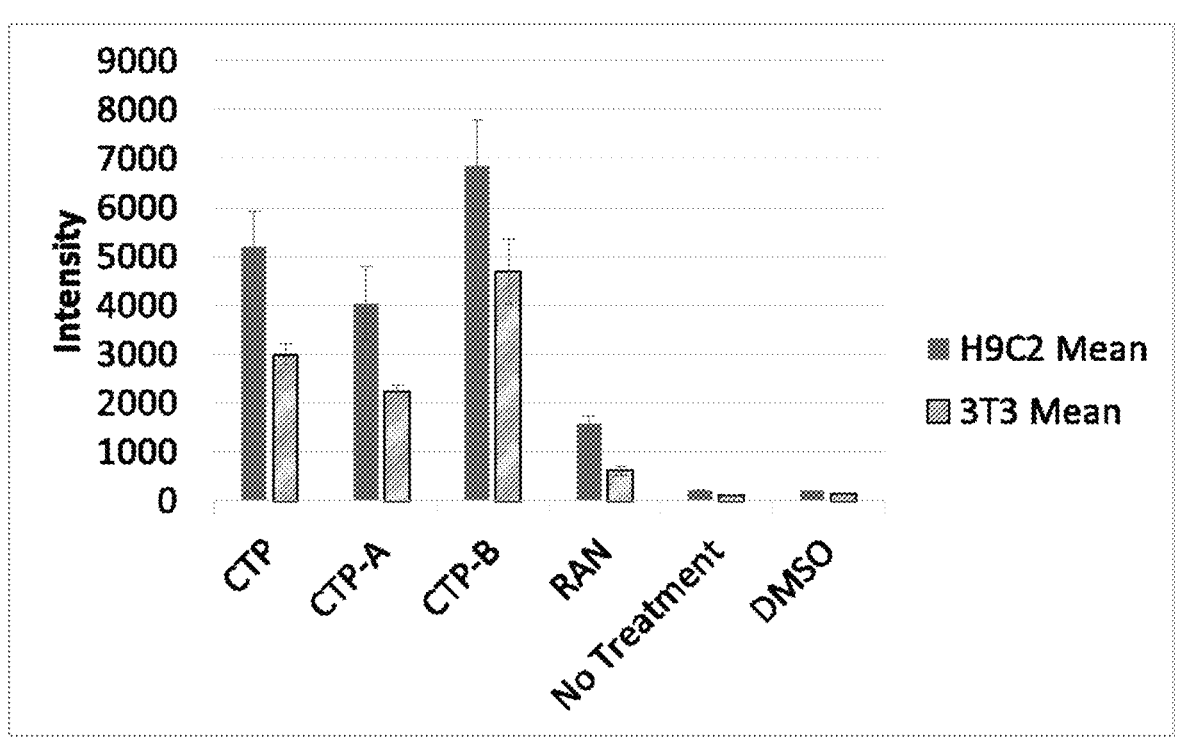
Figure 2E:
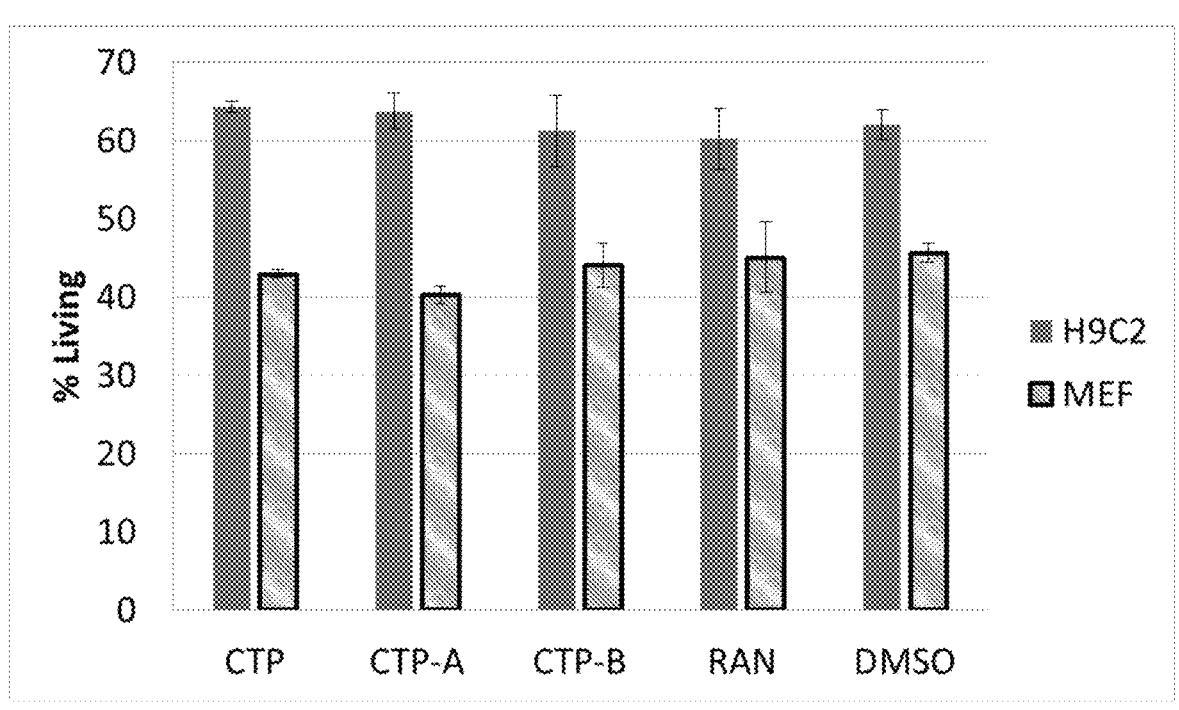

As shown in FIGS. 2A-2E, shorter, linear versions of the cardiac-specific targeting peptide (APWHLSSQYSRT; SEQ ID NO: 1) were able to efficiently transduce the three cell lines tested. Across all three cell lines, the linear 6-amino acid C-terminal peptide variant transduced cells at least as well as the full-length peptide (compare $CTP_{6aa}$ to CTP in FIGS. 2A-2D). Cyclization of the 6-amino acid peptide variants decreased the transduction efficiency of H9C2 cells considerably (FIGS. 2A-2B). Compared to the full-length peptide and DMSO control, transduction of H9C2 cells and MEFs with the linear 6 amino acid C-terminal peptide variants did not alter cell viability (FIG. 2E).

These results demonstrated that the six C-terminal amino acid residues (SQYSRT; SEQ ID NO: 5) are sufficient to confer the cell penetrating ability of the 12-amino acid, full-length cardiac-specific targeting peptide (APWHLSSQYSRT; SEQ ID NO: 1).

Example 3—Delivery of Rhodamine Cargo to Cardiomyocytes Via Conjugation to the C-Terminus of the Cardiac-Specific Targeting Peptide This example describes the use of the cardiac-specific targeting peptide via conjugation at the C-terminus to deliver a rhodamine cargo to the intracellular compartments of cardiomyocytes.

The cardiac-specific targeting peptide was synthesized in the University of Pittsburgh Peptide Synthesis Facility and labeled at the N-terminus with carboxyfluorescein (green), and with rhodamine (red) at the C-terminus through an ester linkage. Beating cardiomyocytes derived from human induced pluripotent stem cells (iPSC) were then incubated with the dual labeled peptide for 30 minutes at 37° C., washed 3× with PBS and immediately thereafter, live cell imaging was performed using confocal microscopy.

Figure 3A:
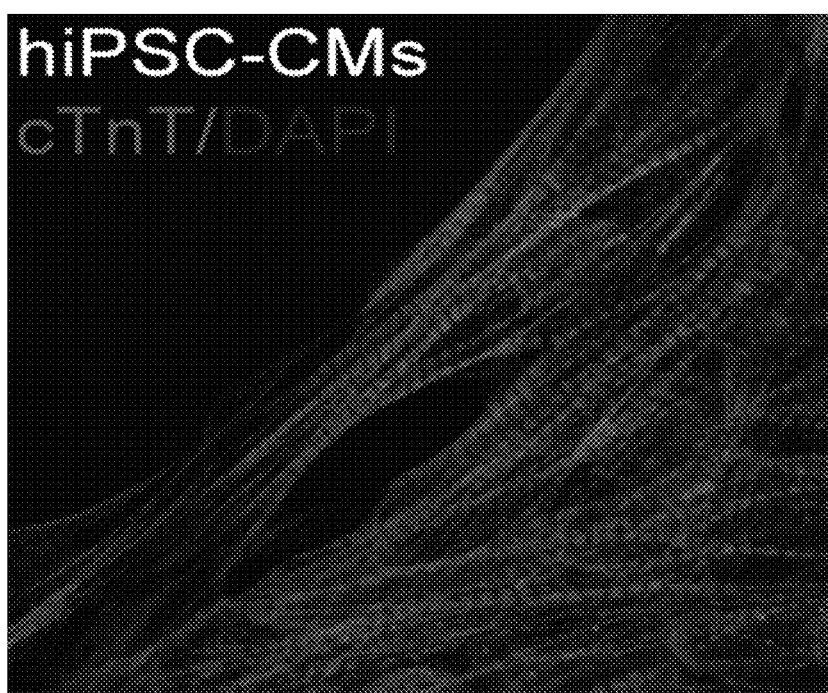
FIGS. 3A-3D show delivery of a rhodamine cargo to the intracellular compartments of cardiomyocytes when the rhodamine cargo is conjugated at the C-terminus of full-length CTP (e.g., $CTP_{6aa}$). Immunohistochemical characterization of human iPSC derived beating cardiomyocytes transduced with a dual-labeled carboxyfluorescein (green)
Figure 3B:
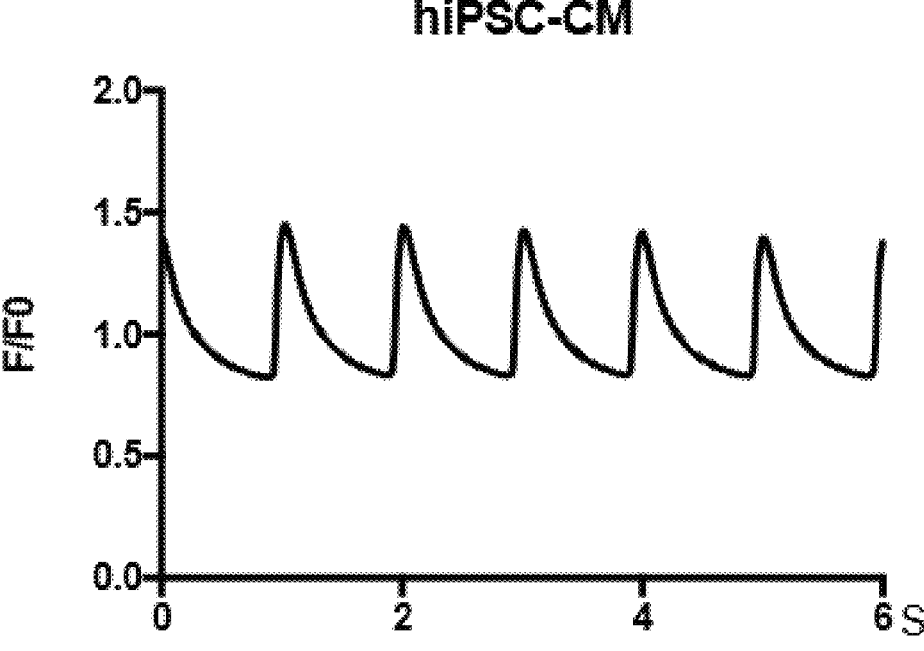
Figure 3C:
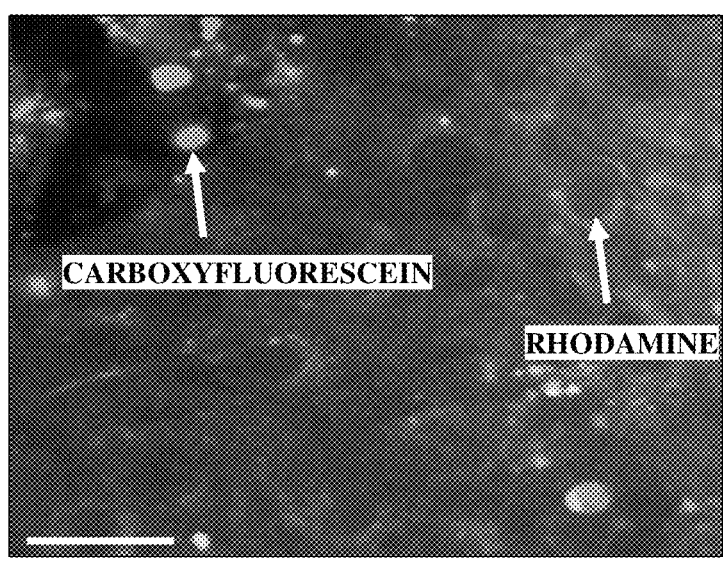
Figure 3D:
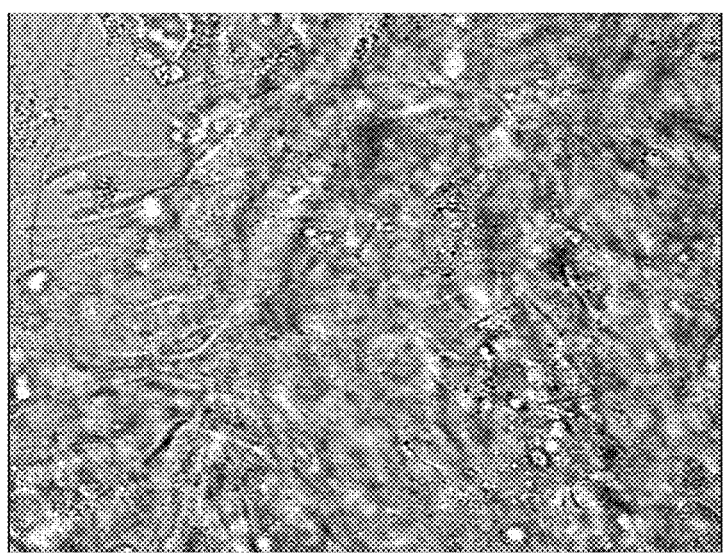
Figure 4:
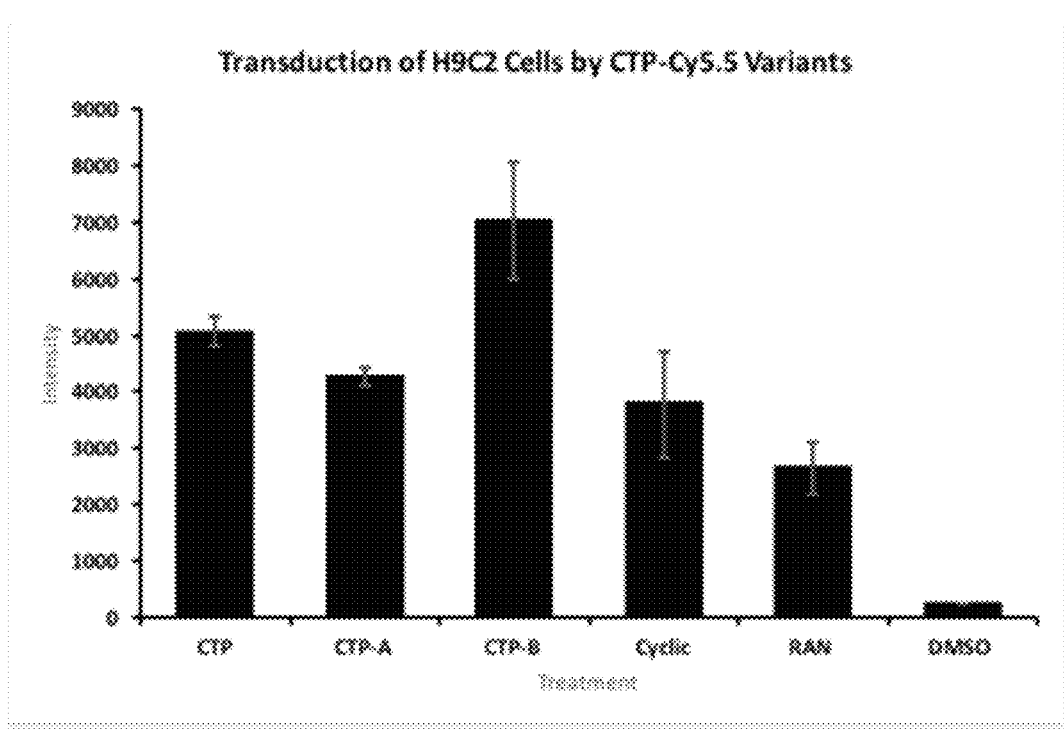
FIG. 4 is a series of bar graphs that show the transduction efficiencies of H9C2 cells incubated with Cy5.5 labeled cardiac-specific targeting peptide variants. CTP (Full Length): $NH_2$-APWHLSSQYSRT-COOH (SEQ ID NO: 1); CTP-A: $NH_2$-APWHLS-COOH (SEQ ID NO: 24); CTP-B: $NH_2$-SQYSRT-COOH ($CTP_{6aa}$; SEQ ID NO: 5); cyclic: cyclized version of the peptide; RAN: a random, linear, 12-amino acid peptide (RAN: $NH_2$-STLMKFCYVEQN-COOH (SEQ ID NO: 26)); DMSO: Dimethyl sulfoxide.

As shown in FIG. 3C, the dual labeled peptide successfully entered the beating human iPSC derived cardiomyocytes, and also that ester-linkage of a cargo to the C-terminus of the cardiac-specific targeting peptide resulted in delivery of the cargo to intracellular compartments due to cleavage of the ester linkage by intracellular esterase(s). FIG. 3C demonstrates that the rhodamine (red) moiety conjugated to the C-terminus of CTP remained inside the cells while the carboxyfluorescein (green) moiety was expelled. Therefore, the data showed that conjugation the rhodamine cargo to the C-terminus of the cardiac-specific targeting peptide (e.g., $CTP_{6aa}$) delivered the cargo inside of cells, while the cargo conjugated to the N-terminus was ejected, which in effect, worked as an internal control.

These results demonstrated that the C-terminus of the cardiac-specific targeting peptide, when conjugated via an ester linkage to a cargo, such as rhodamine, successfully delivered the cargo internally to cardiomyocytes.

Example 4—Uptake of Cy5.5-Labeled CTP by Myocardial Tissue

Figure 5:
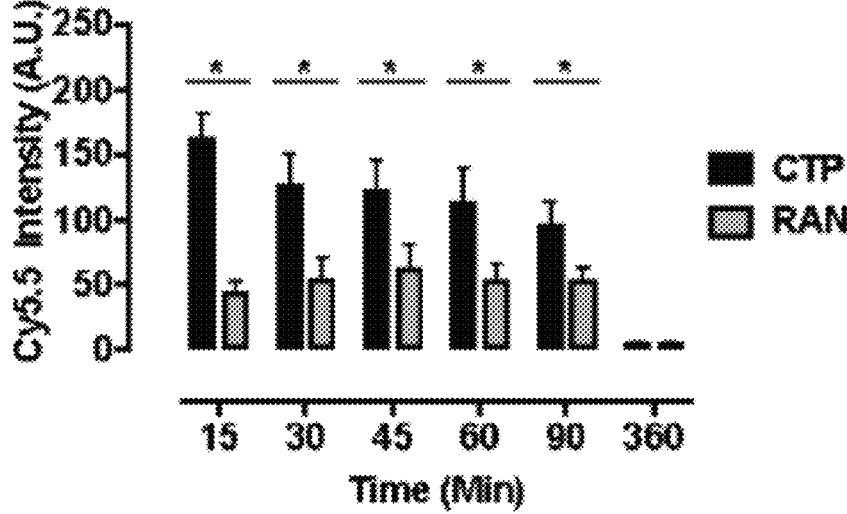
FIG. 5 is a bar graph showing Cy5.5 intensity (arbitrary units ("AU")) in mouse myocardial tissue at various time points (15, 30, 45, 60, 90 or 360 minutes) post-injection of CTP-Cy5.5 or a control random peptide sequence fused to Cy5.5 (RAN-Cy5.5).

In order to analyze the rate of uptake of labeled CTP peptides by myocardial tissue, 6- to 8-week-old wild-type CD1 mice were injected intravenously with a Cy5.5-labeled CTP (CTP-Cy5.5) or a control 12 amino acid random peptide sequence labeled with Cy5.5 (RAN-Cy5.5) at a dose of 10 mg/kg. The peptides were allowed to circulate for 15, 30, 45, 60, 90, or 360 min, after which mice were euthanized, fixed with 3 mL of 10% formalin, and heart tissue was dissected out. Tissue was fixed and embedded in paraffin, and sectioned. The sections were cross-stained with nuclear stain 40,6-diamidino-2-phenylindole (DAPI) and mounted, and fluorescent microscopy was performed. Fluorescence was quantified using ImageJ (National Institute of Health, Bethesda, MD, USA). All time-points and peptides were run in triplicate. Robust uptake of CTP-Cy5.5 was observed, peaking at 15 minutes post injection (FIG. 5). Significantly more uptake of CTP-Cy5.5 was observed at each time point compared to uptake of RAN-Cy5.5.

Figure 6A:
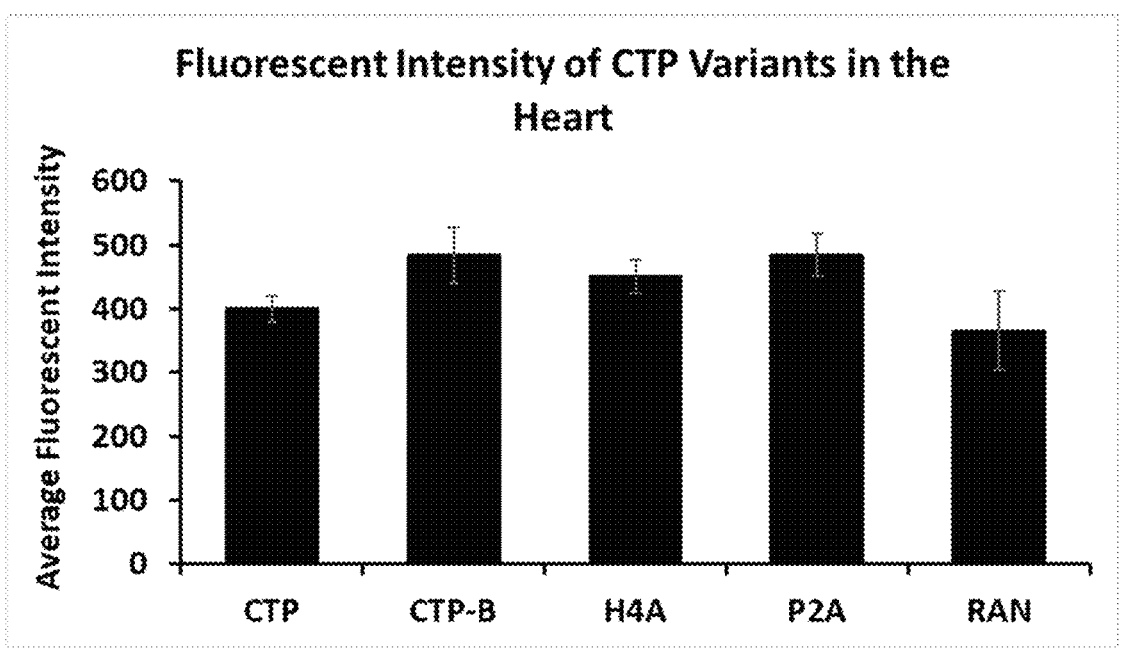
FIG. 6A and FIG. 6B are bar graphs showing average fluorescent intensity measured in heart tissue injected with CTP constructs (CTP, CTP-B, H4A, or P2A) or random control peptide sequence (RAN).
Figure 6B:
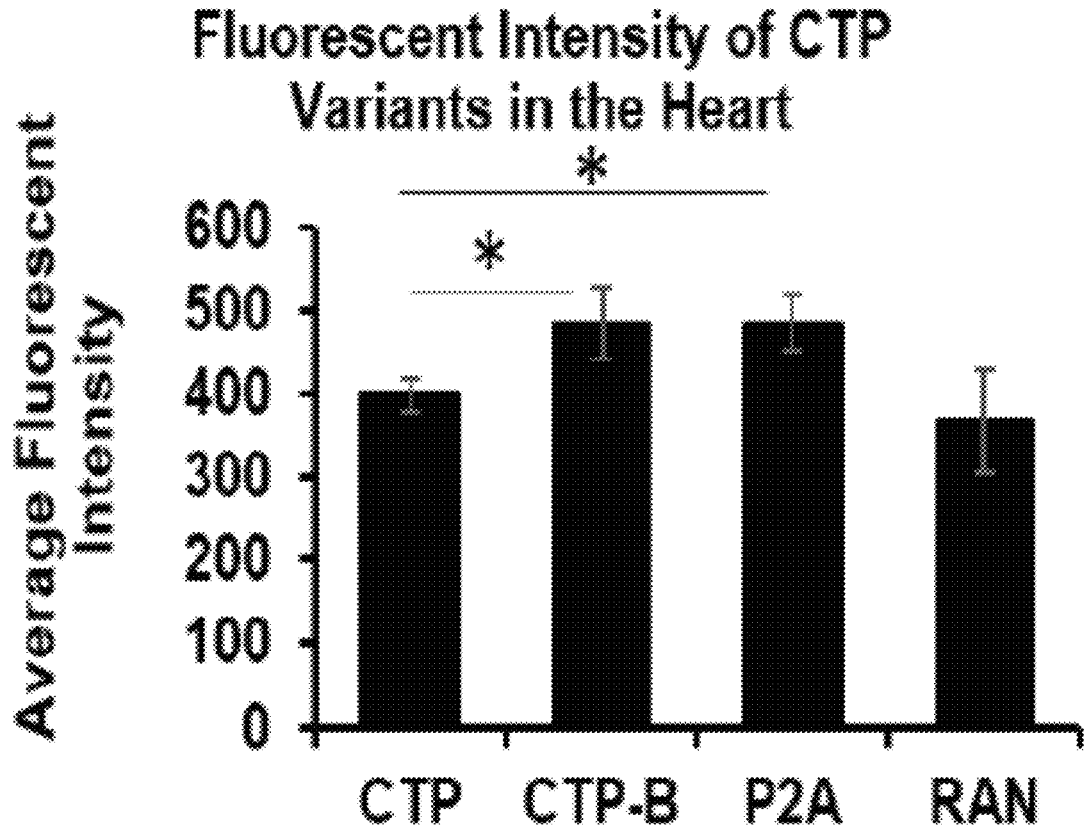

Additionally, fluorescently-labeled CTP variants (CTP, CTP-B, H4A, P2A) or fluorescently-labeled random peptide sequence (RAN) were injected into mice and fluorescence intensity was measured in fixed myocardial tissue. Mice were injected with peptides, and, 15 minutes after injection, heart tissue was dissected, cryosectioned, stained, and analyzed for fluorescence intensity. Results are shown in FIG. 6A and FIG. 6B. Results in FIG. 6B show that fluorescence intensity in myocardial tissue was significantly greater after injection of CTP-B or P2A compared to CTP. These results demonstrate that CTP peptides are taken up rapidly by myocardial tissue (reaching peak uptake 15 minutes after injection) and that CTP-B and alanine peptide variants show superior uptake compared to random peptide sequence and CTP.

Example 5—Amiodarone-CTP for Treating Atrial and/or Ventricular Arrhythmias

Solid phase peptide synthesis (SPPS) of the Amiodarone-CTP peptides is performed with synthesis of the CTP peptides on Rink Amide MBHA resin using Fluorenylmethyloxycarbonyl (FMOC) chemistry with Oxyma/DIC (Ethyl-(2Z)-2-cyano-2-hydroxyiminoacetate/N,N Diisopropylcarbodiimide) activation on a Liberty CEM microwave synthesizer. After completion of the peptide chain assembly, the N-terminal amino group of the $NH_2$-CTP-MBHA resin is conjugated with 6-(Fmoc-amino)-hexanoic acid in DIPEA/TBTU/Hobt/DMF overnight at room temperature. Next, the FMOC-group is removed from the FMOC-hexanoyl-CTP peptides-MBHA resin using 20% Piperidine/DMF for 30 minutes at room temperature. Amiodarone-HCL (Sigma Aldrich) then undergoes a microwave assisted coupling to the free N-terminus of the $NH_2$-hexanoyl-CTP peptides-MBHA resin through an imine linkage (Schiff base). Cleavage of Amiodarone-hexanoyl-CTP peptides-MBHA resin is accomplished using TFA/scavengers for 2 hours at room temperature, and then precipitated with Diethyl Ether. Residual scavengers are extracted from the crude peptide by three rounds of ether washes.

Samples are centrifuged to separate components. The resulting crude Amiodarone-hexanoyl-CTP peptides-CONH2 peptide is then air dried and purified by preparative C-5 RP-HPLC on a Waters Delta Prep 4000 chromatography system using standard Acetonitrile/0.1% TFA gradient conditions. Analytical C-5 RP-HPLC characterization on a Waters Alliance chromatography system followed by MALDI-Tof analysis on an Applied Biosystems Voyager workstation is used to confirm the expected purity and mass of the final product. Equilibration of the purified Amiodarone-hexanoyl-CTP peptides in aqueous solution is followed by analytical reversed phase HPLC monitoring in order to verify the in-vitro release of Amiodarone via hydrolysis of the Schiff base.

Example 6—Neuregulin-1β-CTP for Treatment of SHF

Neuregulin-1β along with its receptors (ErbB2-4 is required for normal cardiac development and has been shown to reduce apoptosis, myocardial fibrosis and reduce infarct size in animal models of diabetes as well as infarction. A few small clinical trials have also shown efficacy of parenteral treatment with recombinant human Neuregulin-1β in patients with SHF. However, progress in bringing this therapy to the clinic has been hampered by significant liver toxicity as well as hypoglycemia.

This example provides a fusion protein of Neuregulin-1β and CTP peptides, with CTP downstream of Neuregulin-1β or attached to its C-terminus. Primers are designed for Neuregulin-1β with sequence of CTP added to the reverse sequence. The combined fusion protein sequence is generated by PCR using mouse genomic DNA extracted from Lungs, Liver or Kidneys. Standard cloning techniques are used to blunt-end ligate the product into a cloning T7 plasmid which is then used to transform BL21 bacterial cells. Colonies that emerge carrying the relevant antibiotic resistance are sequenced and the ones carrying the right sequence, expanded and preserved as the transformed cells of choice. For protein production, these cells are grown in large scale (~500-1000 ml) culture medium and induced to produce the fusion protein under Isopropyl-β-D-thiogalactoside stimulation. The protein is isolated using His-tag and His-coated beads and characterized by Western blot.

INCORPORATION BY REFERENCE

The entire disclosure of each of the patent and scientific documents referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

---

What is claimed is:

1. A compound consisting of a peptide covalently linked, via an ester linkage, a disulfide linker, a peptide bond, a thioester bond, or a carbamate bond, to a cargo selected from the group consisting of: a nucleic acid, a carbohydrate, a lipid, a small molecule, or a combination thereof, wherein the peptide consists of the amino acid sequence of SQYSRT (SEQ ID NO: 5).

2. The compound of claim 1, wherein the cargo is a small molecule.

3. The compound of claim 2, wherein the small molecule is linked upstream of the N-terminus of the peptide.

4. The compound of claim 1, wherein the cargo is amiodarone.

5. The compound of claim 1, wherein the peptide is cyclized.

6. A method of selectively delivering a cargo into a cardiac tissue of a subject, the method comprising administering the compound of claim 1 to the subject.

7. A method of treating a human subject suffering from a cardiac condition selected from the group consisting of atrial arrhythmia and ventricular arrhythmia, the method comprising administering to the subject a therapeutically effective amount of a composition comprising a compound consisting of a peptide covalently linked via an ester linkage, a disulfide linker, a peptide bond, a thioester bond, or a carbamate bond to an anti-arrhythmic compound, wherein the peptide consists of the amino acid sequence of SQYSRT (SEQ ID NO: 5).

8. The method of claim 7, wherein the atrial arrhythmia or ventricular arrhythmia is selected from the group consisting of atrial fibrillation, premature ventricular contractions, ventricular tachycardia, and ventricular fibrillation.

* * * * *

SEQUENCE LISTING

```
Sequence total quantity: 35
SEQ ID NO: 1            moltype = AA  length = 12
FEATURE                 Location/Qualifiers
REGION                  1..12
                        note = Description of Artificial Sequence: Cardiac
                         Targeting Peptide
source                  1..12
                        mol_type = protein
                        organism = synthetic construct
SEQUENCE: 1
APWHLSSQYS RT                                                         12

SEQ ID NO: 2            moltype = AA  length = 12
FEATURE                 Location/Qualifiers
REGION                  1..12
                        note = Description of Artificial Sequence: Cardiac
                         Targeting Peptide (CTP-P2A)
source                  1..12
                        mol_type = protein
                        organism = synthetic construct
```

```
SEQUENCE: 2
AAWHLSSQYS RT                                                        12

SEQ ID NO: 3           moltype = AA  length = 6
FEATURE                Location/Qualifiers
REGION                 1..6
                       note = Description of Artificial Sequence: Cardiac
                        Targeting Peptide (CTP-B), Amiodarone Conjugate
BINDING                1
                       note = Amiodarone is bound to N-terminal amino acid
source                 1..6
                       mol_type = protein
                       organism = synthetic construct
SEQUENCE: 3
SQYSRT                                                               6

SEQ ID NO: 4           moltype =   length =
SEQUENCE: 4
000

SEQ ID NO: 5           moltype = AA  length = 6
FEATURE                Location/Qualifiers
REGION                 1..6
                       note = Description of Artificial Sequence: Cardiac
                        Targeting Peptide (CTP-B)
source                 1..6
                       mol_type = protein
                       organism = synthetic construct
SEQUENCE: 5
SQYSRT                                                               6

SEQ ID NO: 6           moltype = AA  length = 6
FEATURE                Location/Qualifiers
REGION                 1..6
                       note = Description of Artificial Sequence: Cardiac
                        Targeting Peptide
VARIANT                3
                       note = Ala, Trp, or Tyr
VARIANT                6
                       note = Thr or Ala
source                 1..6
                       mol_type = protein
                       organism = synthetic construct
SEQUENCE: 6
SQXSRX                                                               6

SEQ ID NO: 7           moltype = AA  length = 6
FEATURE                Location/Qualifiers
REGION                 1..6
                       note = Description of Artificial Sequence: Cardiac
                        Targeting Peptide
VARIANT                6
                       note = Ala
source                 1..6
                       mol_type = protein
                       organism = synthetic construct
SEQUENCE: 7
SQASRX                                                               6

SEQ ID NO: 8           moltype = AA  length = 6
FEATURE                Location/Qualifiers
REGION                 1..6
                       note = Description of Artificial Sequence: Cardiac
                        Targeting Peptide
VARIANT                6
                       note = Trp
source                 1..6
                       mol_type = protein
                       organism = synthetic construct
SEQUENCE: 8
SQWSRX                                                               6

SEQ ID NO: 9           moltype = AA  length = 6
FEATURE                Location/Qualifiers
REGION                 1..6
                       note = Description of Artificial Sequence: Cardiac
                        Targeting Peptide
VARIANT                6
                       note = Tyr
```

-continued

```
source                  1..6
                        mol_type = protein
                        organism = synthetic construct
SEQUENCE: 9
SQYSRX                                                              6

SEQ ID NO: 10           moltype = AA   length = 6
FEATURE                 Location/Qualifiers
REGION                  1..6
                        note = Description of Artificial Sequence: Cardiac
                         Targeting Peptide
source                  1..6
                        mol_type = protein
                        organism = synthetic construct
SEQUENCE: 10
SQASRT                                                              6

SEQ ID NO: 11           moltype = AA   length = 6
FEATURE                 Location/Qualifiers
REGION                  1..6
                        note = Description of Artificial Sequence: Cardiac
                         Targeting Peptide
source                  1..6
                        mol_type = protein
                        organism = synthetic construct
SEQUENCE: 11
SQWSRT                                                              6

SEQ ID NO: 12           moltype =    length =
SEQUENCE: 12
000

SEQ ID NO: 13           moltype =    length =
SEQUENCE: 13
000

SEQ ID NO: 14           moltype =    length =
SEQUENCE: 14
000

SEQ ID NO: 15           moltype =    length =
SEQUENCE: 15
000

SEQ ID NO: 16           moltype = AA   length = 6
FEATURE                 Location/Qualifiers
REGION                  1..6
                        note = Description of Artificial Sequence: Cardiac
                         Targeting Peptide
VARIANT                 4..5
                        note = Xaa can be any naturally occurring amino acid
source                  1..6
                        mol_type = protein
                        organism = synthetic construct
SEQUENCE: 16
SQYXXT                                                              6

SEQ ID NO: 17           moltype = AA   length = 6
FEATURE                 Location/Qualifiers
REGION                  1..6
                        note = Description of Artificial Sequence: Cardiac
                         Targeting Peptide
VARIANT                 2
                        note = Xaa can be any naturally occurring amino acid
VARIANT                 5
                        note = Xaa can be any naturally occurring amino acid
source                  1..6
                        mol_type = protein
                        organism = synthetic construct
SEQUENCE: 17
SXYSXT                                                              6

SEQ ID NO: 18           moltype = AA   length = 6
FEATURE                 Location/Qualifiers
REGION                  1..6
                        note = Description of Artificial Sequence: Cardiac
                         Targeting Peptide
VARIANT                 2
                        note = Xaa can be any naturally occurring amino acid
```

-continued

```
VARIANT                  4
                         note = Xaa can be any naturally occurring amino acid
source                   1..6
                         mol_type = protein
                         organism = synthetic construct
SEQUENCE: 18
SXYXRT                                                                    6

SEQ ID NO: 19            moltype = AA   length = 6
FEATURE                  Location/Qualifiers
REGION                   1..6
                         note = Description of Artificial Sequence: Cardiac
                          Targeting Peptide
VARIANT                  1
                         note = Xaa can be any naturally occurring amino acid
VARIANT                  5
                         note = Xaa can be any naturally occurring amino acid
source                   1..6
                         mol_type = protein
                         organism = synthetic construct
SEQUENCE: 19
XQYSXT                                                                    6

SEQ ID NO: 20            moltype = AA   length = 6
FEATURE                  Location/Qualifiers
REGION                   1..6
                         note = Description of Artificial Sequence: Cardiac
                          Targeting Peptide
VARIANT                  2
                         note = Xaa can be any naturally occurring amino acid
source                   1..6
                         mol_type = protein
                         organism = synthetic construct
SEQUENCE: 20
SXYSRT                                                                    6

SEQ ID NO: 21            moltype = AA   length = 6
FEATURE                  Location/Qualifiers
REGION                   1..6
                         note = Description of Artificial Sequence: Cardiac
                          Targeting Peptide
VARIANT                  1
                         note = Xaa can be any naturally occurring amino acid
source                   1..6
                         mol_type = protein
                         organism = synthetic construct
SEQUENCE: 21
XQYSRT                                                                    6

SEQ ID NO: 22            moltype = AA   length = 6
FEATURE                  Location/Qualifiers
REGION                   1..6
                         note = Description of Artificial Sequence: Cardiac
                          Targeting Peptide
VARIANT                  4
                         note = Xaa can be any naturally occurring amino acid
source                   1..6
                         mol_type = protein
                         organism = synthetic construct
SEQUENCE: 22
SQYXRT                                                                    6

SEQ ID NO: 23            moltype =    length =
SEQUENCE: 23
000

SEQ ID NO: 24            moltype = AA   length = 6
FEATURE                  Location/Qualifiers
REGION                   1..6
                         note = Description of Artificial Sequence: Cardiac
                          Targeting Peptide (CTP-A)
source                   1..6
                         mol_type = protein
                         organism = synthetic construct
SEQUENCE: 24
APWHLS                                                                    6

SEQ ID NO: 25            moltype = AA   length = 12
FEATURE                  Location/Qualifiers
```

```
REGION                  1..12
                        note = Cardiac Targeting Peptide (CTP-P2A), Amiodarone
                         Conjugate
BINDING                 1
                        note = Amiodarone is bound to N-terminal amino acid
source                  1..12
                        mol_type = protein
                        organism = synthetic construct
SEQUENCE: 25
AAWHLSSQYS RT                                                                    12

SEQ ID NO: 26           moltype = AA  length = 12
FEATURE                 Location/Qualifiers
REGION                  1..12
                        note = Description of Artificial Sequence: Cardiac
                         Targeting Peptide (H4A)
source                  1..12
                        mol_type = protein
                        organism = synthetic construct
SEQUENCE: 26
APWALSSQYS RT                                                                    12

SEQ ID NO: 27           moltype = AA  length = 12
FEATURE                 Location/Qualifiers
REGION                  1..12
                        note = Description of Artificial Sequence: Cardiac
                         Targeting Peptide (L5A)
source                  1..12
                        mol_type = protein
                        organism = synthetic construct
SEQUENCE: 27
APWHASSQYS RT                                                                    12

SEQ ID NO: 28           moltype = AA  length = 12
FEATURE                 Location/Qualifiers
REGION                  1..12
                        note = Description of Artificial Sequence: Cardiac
                         Targeting Peptide (S6A)
source                  1..12
                        mol_type = protein
                        organism = synthetic construct
SEQUENCE: 28
APWHLASQYS RT                                                                    12

SEQ ID NO: 29           moltype = AA  length = 12
FEATURE                 Location/Qualifiers
REGION                  1..12
                        note = Description of Artificial Sequence: Cardiac
                         Targeting Peptide (S7A)
source                  1..12
                        mol_type = protein
                        organism = synthetic construct
SEQUENCE: 29
APWHLSAQYS RT                                                                    12

SEQ ID NO: 30           moltype = AA  length = 12
FEATURE                 Location/Qualifiers
REGION                  1..12
                        note = Description of Artificial Sequence: Cardiac
                         Targeting Peptide (Q8A)
source                  1..12
                        mol_type = protein
                        organism = synthetic construct
SEQUENCE: 30
APWHLSSAYS RT                                                                    12

SEQ ID NO: 31           moltype = AA  length = 12
FEATURE                 Location/Qualifiers
REGION                  1..12
                        note = Description of Artificial Sequence: Cardiac
                         Targeting Peptide (Y9A)
source                  1..12
                        mol_type = protein
                        organism = synthetic construct
SEQUENCE: 31
APWHLSSQAS RT                                                                    12

SEQ ID NO: 32           moltype = AA  length = 12
FEATURE                 Location/Qualifiers
```

-continued

```
REGION                    1..12
                          note = Description of Artificial Sequence: Cardiac
                          Targeting Peptide (S10A)
source                    1..12
                          mol_type = protein
                          organism = synthetic construct
SEQUENCE: 32
APWHLSSQYA RT                                                              12

SEQ ID NO: 33             moltype = AA  length = 12
FEATURE                   Location/Qualifiers
REGION                    1..12
                          note = Description of Artificial Sequence: Cardiac
                          Targeting Peptide (R11A)
source                    1..12
                          mol_type = protein
                          organism = synthetic construct
SEQUENCE: 33
APWHLSSQYS AT                                                              12

SEQ ID NO: 34             moltype = AA  length = 12
FEATURE                   Location/Qualifiers
REGION                    1..12
                          note = Description of Artificial Sequence: Cardiac
                          Targeting Peptide (T12A)
source                    1..12
                          mol_type = protein
                          organism = synthetic construct
SEQUENCE: 34
APWHLSSQYS RA                                                              12

SEQ ID NO: 35             moltype = AA  length = 12
FEATURE                   Location/Qualifiers
REGION                    1..12
                          note = Description of Artificial Sequence: Cardiac
                          Targeting Peptide (W3A)
source                    1..12
                          mol_type = protein
                          organism = synthetic construct
SEQUENCE: 35
APAHLSSQYS RT                                                              12
```